(12) United States Patent
Kakimoto et al.

(10) Patent No.: US 7,807,867 B2
(45) Date of Patent: Oct. 5, 2010

(54) GENE ENCODING PROTEIN INVOLVED IN CYTOKININ SYNTHESIS

(75) Inventors: Tatsuo Kakimoto, Osaka (JP); Hitoshi Sakakibara, Saitama (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 480 days.

(21) Appl. No.: 11/398,550

(22) Filed: Apr. 6, 2006

(65) Prior Publication Data

US 2006/0236431 A1    Oct. 19, 2006

Related U.S. Application Data

(62) Division of application No. 10/471,040, filed as application No. PCT/JP02/02315 on Mar. 12, 2002, now abandoned.

(30) Foreign Application Priority Data

Mar. 12, 2001    (JP)   ............... 2001-69489

(51) Int. Cl.
    *C12N 15/29*      (2006.01)
    *C12N 15/82*      (2006.01)
    *C12N 5/04*      (2006.01)
    *C12N 15/87*      (2006.01)
(52) U.S. Cl. ...................... 800/278; 800/290; 536/23.1; 536/23.6; 435/320.1; 435/419
(58) Field of Classification Search ....................... None
See application file for complete search history.

(56) References Cited

U.S. PATENT DOCUMENTS 5,689,042 A    11/1997    Amasino et al.

FOREIGN PATENT DOCUMENTS

EP    0 911 412    4/1999
EP    1 033 405    9/2000

OTHER PUBLICATIONS

Roeckel et al (1997, Transgenic Research 6(2):133-141).*
Sa et al (2002, Transgenic Research 11(3):269-278).*
Bowie et al, Science 247:1306-1310, 1990.*
McConnell et al, Nature 411 (6838):709-713, 2001.*
Fourgoux-Nicol et al (1999, Plant Molecular Biology 40 :857-872).*
Huang et al (2000, NCBI Accession No. AC068809).*
Komamine, "Encyclopedia of plant biotechnology," 1990, pp. 91-92 and pp. 190-191.
Office Action issued by Japanese Patent Office for JP Appln. No. 2002-571873.
Kaneko et al., "Structural Analysis of *Arabidopsis thaliana* Chromosome 3. II. Sequence Features of the 4,251,695 bp Regions Covered by 90 P1, TAC and BAC Clones," DNA Research, 2000, vol. 7, pp. 217-221.

Sato et al., "Structural Analysis of *Arabidopsis thaliana* Chromosome 3. I. Sequence Features of the Regions of 4,504,864 bp Covered by Sixty P1 and TAC Clones," DNA Research, 2000, vol. 7, pp. 131-135.
Ecker, et al., "Sequence and analysis of chromosome 1 of the plant*Arabidopsis thaliana*," Nature, vol. 408, Dec. 14, 2000, pp. 816-820.
Bevan et al., "Hypothetical protein F22K18.150-*Arabidopsis thaliana*," Protein Sequence Database Accession No. T05569, Aug. 26, 1999.
Obermaier et al., "tRNA isopentenyl transferase-like protein-*Arabidopsis thaliana*," Protein Sequence Database Accession No. T48100, Apr. 20, 2000.
MIPS Accession No. AL161561, *Arabidopsis thaliana* DNA chromosome 4, contig fragment No. 61, Mar. 16, 2000.
MIPS Accession No. AL035356, *Arabidopsis thaliana* DNA chromosome 4, BAC clone F22K18, Feb. 3, 2000.
MIPS Accession No. AL163816, *Arabidopsis thaliana* DNA chromosome 3, BAC clone T20010, Apr. 13, 2000.
Lin et al., "*Arabidopsis thaliana* chromosome 1, BAC T26J14 genomic sequence," Genomic Research Accession No. AC011915, Jan. 19, 2001.
Town et al., "*Arabidopsis thaliana* chromosome 1 BAC F2J7 genomic sequence," Genomic Research Accession No. AC079281, Jan. 19, 2001.
Crespi et al., "The *fas* Operon of *Rhodococcus fascians* Encodes New Genes Required for Efficient Fasciation of Host Plants," Journal of Bacteriology, May 1994, pp. 2492-2501.
Powell et al., "Nucleotide sequence and expression of a *Pseudomonas savastanoi* cytokinin biosynthetic gene: homology with*Agrobacterium tumefaciens tmr* and *tzs* loci," Nucleic Acids Research, vol. 14, No. 6, 1986, pp. 2555-2565.
Beaty et al., "*Tzs*, a nopaline TI plasmid gene from *Agrobacterium tumefaciens* associated with *trans*-zeatin biosynthesis," Mol. Gen. Genet., vol. 203, 1986, pp. 274-280.
Lichter et al., "The Genes Involved in Cytokinin Biosynthesis in*Erwinia herbicola* pv. gypsophilae: Characterization and Role in Gall Formation," Journal of Bacteriology, vol. 177, No. 15, Aug. 1995, pp. 4457-4465.
Burland et al., "Analysis of the *Escherichia coli* genome VI: DNA sequence of the region from 92.8 through 100 minutes," Nucleic Acids Research, vol. 23, No. 12 , 1995, pp. 2105-2119.
Blackwell et al., "Cytokinin Biosynthesis by Extracts of Zea Mays," Phytochemistry, vol. 35, No. 2, 1994, pp. 339-342.
Chen et al., "Cytokinin Biosynthesis in a Cell-Free System from Cytokinin-Autotropic Tobacco Tissue Cultures," FEBS Letters, vol. 107, No. 1, Nov. 1979, pp. 15-20.
Takei et al., "Identification of Genes Encoding Adenylate Isopentenyltransferase, a Cytokinin Biosynthesis Enzyme, in*Arabidopsis thaliana*," The Journal of Biological Chemistry, vol. 276, No. 28, Jul. 13, 2001, pp. 26405-26410.

(Continued)

*Primary Examiner*—Stuart F. Baum
(74) *Attorney, Agent, or Firm*—Drinker Biddle & Reath LLP

(57) ABSTRACT

A gene is provided that encodes an amino acid sequence indicated in SEQ ID NO. 2, 4, 6, 8, 10, 12 or 14 originating in, for example, *Arabidopsis thaliana*.

10 Claims, 2 Drawing Sheets

OTHER PUBLICATIONS

Kakimoto, "Identification of Plant Cytokinin Biosynthetic Enzymes as Dimethylallyl Diphosphate: ATP/ADP Isopentenyltransferases," Plant Cell Physiol., vol. 42, No. 7, 2001, pp. 677-685.

Sun et al., "The *Arabidopsis AtIPT8*/PGA22 Gene Encodes an Isopentnyl Transferase that is Involved in De Novo Cytokinin Biosynthesis," Plant Physiology, 2003, vol. 131, pp. 167-176, The American Society of Plant Biologists, New York, New York.

Miyawaki et al., "Expression of cytokinin biosynthetic ispentenyltransferase genes in *Arabidopsis*: tissue specificity and regulation by auxin, cytokinin, and nitrate," The Plant Journal, 2004, vol. 37, pp. 128-138, Blackwell Publishing Ltd., UK.

Roeckel et al. (1997, Transgenic Research 6(2):133-141).

Sa et al. (2002, Transgenic Research 11(3):269-278).

Bowie et al., Science 247:1306-1310, 1990.

McConnell et al., Nature 411 (6838):709-713, 2001.

Lin et al. (Jan. 2001, NCBI Accession No. AC011915).

Fourgoux-Nicol et al. (1999, Plant Molecular Biology 40:857-872).

Kaneko et al., GenBank Accession No. AP000419, Feb. 14, 2004, at http://www.ncbi.nlm.nih.gov/entrez/viewer.fcgi?db=nucleotide&val=5832740.

Kaneko et al., GenBank Accession No. BAB02956, Feb. 14, 2004, at http://ww.ncbi.nlm.nih.gov/entrez/viewer.fcgi?db=protein&val=9294617.

Sato et al., GenBank Accession No. BAB02782, Feb. 14, 2004, at http://www.ncbi.nlm.nih.gov/entrez/viewer.fcgi?db=protein&val=9294520.

Sato et al., GenBank Acession No. AB023036, Feb. 14, 2004, at http://www.ncbi.nlm.nih.gov/entrez/viewer.fcgi?db=nucleotide&val=4220635.

Lin et al., GenBank Accession No. AC011915, Jan. 19, 2001, at http://www.ncbi.nlm.nih.gov/entrez/viewer.fcgi?db=nucleotide&val=12324876.

Lin et al., GenBank Acession No. AAG52395, Jan. 19, 2001, at http://www.ncbi.nlm.nih.gov/entrez/viewer.fcgi?db=protein&val=12324885.

Lin et al., GenBank Accession No. AC079281, Jan. 19, 2001, at http://www.ncbi.nlm.nih.gov/entrez/viewer.fcgi?db=nucleotide&val=12321495.

Lin et al., GenBank Accession No. AAG50809, Jan. 19, 2001, at http://www.ncbi.nlm.nih.gov/entrez/viewer.fcgi?db=protein&val=12321506.

Komamine, "Encyclopedia of plant biotechnology," 1990, pp. 91-92 and pp. 190-191 (partial English-language translation).

* cited by examiner

GENE ENCODING PROTEIN INVOLVED IN CYTOKININ SYNTHESIS

CROSS REFERENCE TO RELATED APPLICATIONS

This application is a divisional application of U.S. application Ser. No. 10/471,040, filed Sep. 8, 2003, abandoned, which is a National Phase Application of International Appl. No. PCT/JP02/02315, with an International Filing Date of Mar. 12, 2002 and designating the United States of America, which claims the benefit of Japanese Appl. No. 2001 69489, filed Mar. 12, 2001. Japanese Appl. No. 2001 69489, filed Mar. 12, 2001 is incorporated herein by reference in its entirety for all purposes.

REFERENCE TO A SEQUENCE LISTING

Incorporated herein by reference in its entirety is a Sequence Listing containing SEQ ID NOs: 1-35.

FIELD OF THE INVENTION

The present invention relates to a gene encoding a protein involved in cytokinin synthesis, a method of utilizing that gene, and a method for acquiring that gene.

BACKGROUND ART

Cytokinins are an important type of plant hormone. They have various effects including induction of cell division, formation of new buds, overcoming dormancy of axillary buds, prevention of aging and promotion of enlargement of fruit. Cytokinins have a structure in which a dimethylallyl group (isopentenyl group) bonds to a nitrogen atom at position 6 of adenine or adenosine, or has a structure in which the isopentenyl group is hydroxylated as their basic skeleton. Some bacteria that are pathogenic to plants are known to have cytokinin synthesis enzymes and among these, the cytokinin synthases of IPT and TZS of *Agrobacterium* are known to have activity that transfers the dimethylallyl group of dimethylallyl pyrophosphoric acid (DMAPP) to the nitrogen atom at position 6 of adenosine monophosphate (AMP). This reaction is considered to be the most important step in cytokinin synthesis. However, cytokinin synthesis enzymes possessed by plants and the proteins that encode them have yet to be identified.

DISCLOSURE OF THE INVENTION

Therefore, an object of the present invention is to provide a gene that encodes an enzyme that catalyzes cytokinin synthesis, a protein encoded thereby, and its application. In addition, an object of the present invention is to provide a method for identifying that gene.

The inventors of the present invention found a method for obtaining a novel gene that encodes an enzyme that catalyzes cytokinin synthesis from *Arabidopsis thaliana*, and obtained a novel gene that encodes an enzyme that catalyzes cytokinin synthesis.

Thus, the present invention provides a gene that encodes a protein involved in cytokinin synthesis. More specifically, the protein is a previously unreported enzyme in plants that catalyzes the reaction in which a side chain is introduced at position N6 of the adenine skeleton of cytokinins.

More specifically, the present invention provides a gene that encodes a protein involved in cytokinin synthesis having the amino acid sequence described in SEQ ID NO. 2, 4, 6, 8, 10, 12 or 14. In addition, the present invention provides a gene that encodes a protein involved in cytokinin synthesis having a modified amino acid sequence resulting from the addition and/or deletion of one or a plurality of amino acids and/or substitution by other amino acids in SEQ ID NO. 2, 4, 6, 8, 10, 12 or 14. Moreover, the present invention provides a gene encoding a protein involved in cytokinin synthesis that hybridizes with a nucleic acid described in SEQ ID NO. 1, 3, 5, 7, 9, 11 or 13, and particularly DNA or a portion thereof, under stringent conditions.

The present invention also provides a vector that contains that gene.

Moreover, the present invention provides a host that has been transformed by that vector. This host may be a plant cell or a plant body.

The present invention is also able to provide a production method of a protein involved in cytokinin synthesis by culturing and cultivating the aforementioned host.

In addition, the present invention is able to provide a method for regulating the growth of a plant or plant cells by introducing the aforementioned gene into a plant or plant cells and expressing said gene. Namely, various physiological actions in which cytokinins are involved, such as promotion of the formation of adventitious buds, overcoming the dormancy of lateral buds, prevention of the aging of flowers and leaves and the ripening of fruit, improving the longevity of flowers, maintaining photosynthesis function, promoting the enlargement of fruit, prevention of dropping and control of flowering, can be regulated by expressing this gene.

DESCRIPTION OF THE PREFERRED EMBODIMENTS

Figure 1:
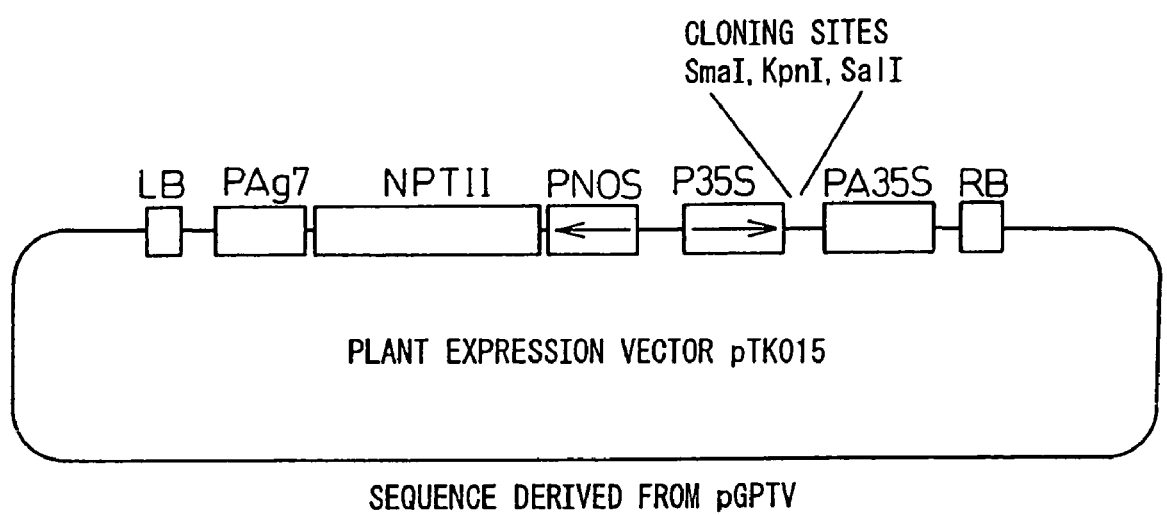
FIG. 1 is a drawing showing the structure of plasmid pTK015.

The inventors of the present invention surmised that the reaction that catalyzes the introduction of an isopentenyl (dimethylallyl) side chain at the N6 position of the adenine skeleton is the rate-limiting step of cytokinin synthesis. Examples of genes that are known to encode isopentenyl group transferases involved in cytokinin synthesis include the ipt (gene4) gene encoded by T-DNA and the tzs gene present in the vir region of the Ti-plasmid of *Agrobacterium tumefaciens*, the ptz gene present in several species of *Pseudomonas*, the ipt gene of *Rhodococcus faciens*, and the etz gene of *Erwinia herbicola*. Among these, the gene products of the tzs and ipt genes of *Agrobacterium*, the etz gene of *Pseudomonas* and the ipt gene of *Rhodococcus* have been demonstrated to have DMAPP:AMP dimethylallyl transferase activity in vitro. In addition to these, many living organisms have enzymes that transfer an isopentenyl group from DMAPP to rRNA. If plant cytokinins are assumed to be synthesized by isopentenylation of the adenine skeleton, then there is the possibility that enzymes that catalyze this reaction may have amino acids in common with the isopentenyl group transferases mentioned above. Therefore, the amino acid sequences of these gene products were first compared to find the amino acid residues preserved therein. The resulting sequence was determined to be GxTxxGK[ST]xxxxx[VLI]xxxxxxx[VLI][VLI]xxDxxQx[57,60][VLI][VLI]xGG[ST] (SEQ ID NO: 35). Here, x indicates an arbitrary amino acid, amino acid residues enclosed in brackets [ ] indicate which one of the amino acid residues contained therein, and [a,b] indicates the number of arbitrary types of amino acid residues greater than or equal to a but less than or equal to b.

The genome sequence of *Arabidopsis thaliana* was searched using a TAIR Pattern Matching program to find the possible genes or estimated gene regions based on this amino acid sequence pattern. The resulting eight genes consisted of AT4g24650 (number of the estimated gene region as determined by the Genome Project), T20010_210 (number of the estimated gene region as determined by the Genome Project), 29375-30301 bp of T16G12 (accession number: AC068809) genome clone, MDB19.12 (number of the estimated gene region as determined by the Genome Project), MVI11.6 (number of the estimated gene region as determined by the Genome Project), T26J14.3 (number of the estimated gene region as determined by the Genome Project), F2J7.12 (number of the estimated gene region as determined by the Genome Project) and AF109376.

Among these eight genes, an estimated gene, AF109376, has been cloned as the cDNA and annotated as being tRNA isopentenyl transferase mRNA. Among the seven remaining genes, T20010_210, MDB19.12, AT4g24650, MVI11.6, T26J14.3 and F2J7.12 have not being isolated as full length cDNA but estimated genes, and annotated to be likely tRNA isopentenyl transferases. 29375-30301 bp of T16G12 (accession number: AC0699089) genome clone is not even annotated.

The genes or estimated genes of AT4g24650, T20010_210, cDNA corresponding to 29375-30301 bp of T16G12 (accession number: AC068809) genome clone, MDB19.12, MVI11.6, T26J14.3 and F2J7.12 are designated AtIPT4, AtIPT3, AtIPT5, AtIPT7, AtIPT8 and AtIPT6. In addition, each of their nucleotide sequences are shown with SEQ ID NOs. 1, 3, 5, 7, 9, 11 and 13, and their corresponding amino acid sequences are indicated with SEQ ID NOs. 2, 4, 6, 8, 10, 12 and 14.

Although the calli of *Arabidopsis thaliana* normally form leaves and buds (to be referred to as shoots) when cytokinins are present in the medium, if cytokinins are not present, it does not form any shoots or even if they are formed, the frequency of formation is extremely low. Therefore, if callus efficiently forms shoots even in the absence of cytokinins when a gene has been introduced and expressed in the callus, the introduced gene can be considered to encode a cytokinin synthase or protein involved in cytokinin reactions.

Alternatively, by expressing the resulting gene using a gene expression system such as *E. coli* or yeast and then measuring the enzyme activity, the resulting gene can be confirmed to encode a cytokinin synthase or protein involved in cytokinin reactions.

On the basis of the above, in the present invention, a gene that encodes a cytokinin synthase or protein involved in cytokinin synthesis of plant origin was isolated and identified for the first time.

In addition, in the present invention, plant cytokinin synthase was found to transfer the DMA group of DMAPP to ATP and ADP.

Examples of a gene of the present invention include that coding for the amino acid sequence described in SEQ ID NO. 2, 4, 6, 8, 10, 12 or 14. However, proteins having an amino acid sequence that has been modified by addition or deletion or a plurality of amino acids, and/or substitution by other amino acids are known to maintain activity similar to the original protein. Thus, a modified gene that encodes a cytokinin synthase or protein involved in cytokinin synthesis activity and has an amino acid sequence that has been modified with respect to an amino acid sequence described in SEQ ID NO. 2, 4, 6, 8, 10, 12 or 14 by addition or deletion of one or a plurality of amino acids and/or substitution by other amino acids, is also included in the present invention.

Here, the degree of this modification is the degree which is possible by means that were commonly known technologies prior to filing of the present patent application, examples of which include site-specific mutagenesis, PCR method and so on. The number of amino acids subject to modification while maintaining the activity of the cytokinin synthase or that relating to cytokinin synthesis is, for example 100 or less, for example 50 or less, preferably 25 or less, and for example 10 or less.

In addition, the present invention also provides a gene composed of DNA that encodes a cytokinin synthase or protein having activity involved in cytokinin synthesis, and which is capable of hybridizing with a nucleic acid having a nucleotide sequence described in SEQ ID NO. 1, 3, 5, 7, 9, 11 or 13, or portion thereof, under stringent conditions. Here, stringent conditions refer to hybridization conditions consisting of 5×SSC and 50° C. Furthermore, as the suitable hybridization temperature varies according to the particular nucleotide sequence and the length of that nucleotide sequence, hybridization can be carried out by suitable selecting the hybridization temperature.

A cDNA library, genomic DNA library and so forth prepared from a plant or microorganism, etc. having cytokinin synthase activity or activity involved in cytokinin synthesis can be used for the source of the gene subjected to the aforementioned hybridization, examples of which include plants such as *Arabidopsis thaliana*, corn, poplar, petunia, tobacco, rice, tomato and eucalyptus plants.

The nucleotide sequence of a gene encoding a cytokinin synthase or protein involved in cytokinin synthesis obtained in this manner has homology of 50% or more, 60% or more, preferably 70% or more or 80% or more, and for example 90% or more, with respect to a nucleotide sequence indicated in SEQ ID NO. 1, 3, 5, 7, 9, 11 or 13.

As will be concretely indicated in the examples, the subject gene encoding a protein having an amino acid sequence indicated in SEQ ID NO. 2, 4, 6, 8, 10, 12 or 14 can be obtained from *Arabidopsis thaliana* in the form of cDNA or genomic DNA.

In addition, DNA encoding a protein having a modified amino acid sequence can be synthesized using commonly used site-specific mutagenesis or PCR method by using DNA having the inherent nucleotide sequence as a base. For example, a DNA fragment containing a desired modification can be obtained by obtaining a DNA fragment in which a modification is desired to be introduced by restriction enzyme treatment of the inherent cDNA or genomic DNA, and then performing site-specific mutagenesis or PCR method using this DNA as a template and a primer containing the desired mutation. Subsequently, this DNA fragment into which the mutation has been introduced should then be coupled with a DNA fragment that encodes another portion of the target protein.

Alternatively, in order to obtain DNA that encodes protein composed of a shortened amino acid sequence, DNA that encodes an amino acid sequence longer than the target amino acid sequence, such as the entire amino acid sequence, should be digested by a desired restriction enzyme and, if the resulting DNA fragment does not encode the entire target amino acid sequence, a DNA fragment composed of the portion of the sequence that is lacking should be synthesized and then coupled to that fragment.

Alternatively, cytokinin synthase or a protein having activity involved in cytokinin synthesis can also be obtained by using antibody to a protein having an amino acid sequence described in SEQ ID NO. 2, 4, 6, 8, 10, 12 or 14, and cytokinin synthase or protein having activity involved in cytokinin synthesis of other organisms can be cloned using antibody.

Thus, the present invention also relates to a recombinant vector, and particularly an expression vector, that contains the aforementioned gene, and to a host transformed by said vector. Procaryotic organisms or eucaryotic organisms can be used as hosts. Examples of prokaryotic organisms include bacteria such as *Escherichia coli* and other *Escherichia* species, *Bacillus subtilis* and other *Bacillus* species as well as other commonly used host microorganisms.

Examples of eucaryotic organisms include lower eucaryotic organisms such as eucaryotic microorganisms in the form of yeasts and molds. Examples of yeasts include *Saccharomyces cerevisiae* and other *Saccharomyces* species, while examples of molds include *Aspergillus oryzae, Aspergillus niger* and other *Aspergillus* species as well as *Penicillium* species. Moreover, plant cells and animal cells may also be used as hosts, examples of which include cells systems of animals cells such as mouse, hamster, monkey or human cells, and more specifically, COS cells, Vero cells, CHO cells, L cells, C127 cells, BALB/c 3T3 cells and Sp-2/0 cells. Examples of plant cells include tobacco and *Arabidopsis* cultured cells as well as cultured cells of poplar, eucalyptus and acacia species.

Moreover, insect cells such as silkworm (*Bombyx mori*) cells or adult silkworms themselves can be used as hosts. In addition, yoga (*Spodoptera frugiprd*) or cabbage looper (*Trichoplusiani*) cells can also be used.

Plasmids, phages, phagemids and viruses (such as Baculovirus (expression in insects) or Vaccinia virus (expression in animal cells)) can be used as expression vectors.

Expression vectors of the present invention contain expression control regions such as promoters, terminators, replication origins and so forth depending on the type of host into which they are to be introduced. Examples of promoters of bacterial expression vectors include lac promoter, examples of yeast promoters include glyceraldehyde 3-phosphate dehydrogenase promoter, PHO5 promoter, adhI promoter and pqk promoter, and examples of mold promoters include amylase promoter and trpC promoter.

In addition, examples of insect promoters include Baculovirus polyhedron promoter, and examples of animal cell promoters include Simian Virus 40 early and late promoters, CMV promoter, HSV-TK promoter or SRα promoter. Examples of plant promoters include the 35S promoter of cauliflower mosaic virus and nopaline synthase promoter, while examples of inductive promoters include glutathione-S-transferase II gene promoter, hsp80 promoter and ribulose 2-phosphate carboxylase small subunit gene promoter.

In addition, preferable modes of the expression vector include, in addition to those described above, those containing enhancers, splicing signals, poly A addition signals or selection markers (for example, dihydrofolic acid reductase genes (methotrexate resistant) and neo genes (G418 resistant)). Furthermore, in the case of using an enhancer, SV40 enhancer, for example, is inserted upstream or downstream from the gene.

Host transformation by an expression vector can be carried out in accordance with ordinary methods well known among persons with ordinary skill in the art, and these methods are described in, for example, Current Protocols in Molecular Biology, John Wiley & Sons Publishing, 1995. Culturing of the transformant can also be carried out in accordance with ordinary methods. Purification of protein involved in cytokinin synthesis from the culture can be carried out in accordance with ordinary methods for isolating and purifying proteins, examples of which include ultrafiltration and various types of column chromatography such as chromatography using Sepharose.

On the basis of the current level of technology, adventitious bud formation can be promoted even in plants such as roses, for which individual regeneration is difficult even by artificial regulation using plant hormones externally added to the medium, by inserting and expressing this gene in a plant by coupling this cDNA or gene under the control of a composite or inductive promoter with a system that uses *Agrobacterium* or a system that uses a particle gun or electroporation and so forth. Moreover, the various physiological actions exhibited by cytokinins in plants, such as lateral bud elongation, prevention of aging, flowering time, promotion of fruit enlargement and prevention of fruit dropping, can be regulated by controlling the expression of a gene that encodes a protein involved in cytokinin synthesis.

The following provides a detailed description of the present invention according to examples. Unless stated otherwise, molecular biological techniques are in accordance with Molecular Cloning (Sambrook, et al., 1989).

Example 1

Search for and Isolation of Genes Encoding Proteins Involved in Cytokinin Synthesis As a result of analyzing the amino acid sequences of the gene products of the tzs gene of *Agrobacterium tumefaciens* (Accession No. X03933-1, Protein ID No. CAA27572.1), the ipt gene of *Agrobacterium tumefaciens* (Accession No. AB025109-1, Protein ID No. BAA76344.1), the ptz gene of *Pseudomonas syringae* (Accession No. X03679-1, Protein ID No. CAA27315.1), the ipt gene of *Rhodococcus faciens* (Accession No. Z29635-4, Protein ID No. CAA82744.1), the dimethylallyl transferase gene of *Erwinia herbicola* (Accession No. Z46375-2, Protein ID No. CAA86510.1) and the delta-2-isopentenyl phosphate (IPP) transferase gene of *Escherichia coli* tRNA (Accession No. U14003-83, Protein ID No. AAA97067.1) using the amino acid sequence comparison software, Clustal V of Macvector 6.5.3, the preserved sequence of GxTxxGK[ST]xxxxx[VLI]xxxxxxx[VLI][VLI] xxDxxQx [57,60][VLI][VLI]xGG[ST] (SEQ ID NO: 35) was found. Here, x indicates an arbitrary amino acid, amino acid residues enclosed in brackets [ ] indicate which one of the amino acid residues contained therein, and [a,b] indicates the number of arbitrary types of amino acid residues greater than or equal to a but less than or equal to b.

Next, in order to isolate those genes or estimated gene regions considered to have this preserved amino acid sequence pattern, a search was made of the genomic database of *Arabidopsis thaliana* using the TAIR Pattern Matching Program. As a result, eight genes consisting of the estimated gene region numbers as designated by the National Genome Project of AT4g24650, T20010_210, MDB19.12, MVI11.6, T26J14.3, F2J7.12, AF109376 and the 29375-30301 bp region of the T16G12 genome clone (Accession No. AC068809) were determined to have the aforementioned preserved amino acid sequence pattern.

Among these eight genes, cDNA has previously been cloned for AF109376 only, and is annotated as tRNA isopentenyl transferase mRNA. However, since the total length cDNA of AT4g24650, T20010_210, MDB19.12, MVI11.6, T26J14.3 and F2J7.12 have not been isolated, they are annotated as probably being tRNA isopentenyl transferases. With respect to the 29375-30301 bp region of the genome clone of T16G12 (Accession No. AC068809), there are even no annotations regarding its estimated function. Namely, the functions of these eight genes are only estimated on the basis of computer analyses, while there have been no experimental analyses whatsoever, and their functions were not known. In addition, their enzyme activity has also not been measured, and their substrates have not been identified.

The nucleotide sequences of AT4g24650 (AtIPT4), T2000_210 (AtIPT3), the cDNA corresponding to the 29375-30301 bp region of the genome clone of T16G12 (Accession No. AC068809) (AtIPT5), MDB19.12 (AtIPT7), MVI11.6 (AtIPT8), T26J14.3 (AtIPT1) and F2J7.12 (AtIPT6) are shown in SEQ. ID NOs. 1, 3, 5, 7, 9, 11 and 13.

In addition, a molecular phylogenetic tree was produced with the Clustal W Program (retrieved from the internet: <URL: http://www.ddbj.nig.ac.jp/E-mail/clustalw-e.htm>, Thompson, et al., 1994, Nucl. Acids Res., 22, 4673-4680), including each of the amino acids encoded by them (SEQ ID NOs. 2, 4, 6, 8, 10, 12 and 14) and homologous amino acid sequences obtained as a result of searching DNA databases (such as the DNA Databank of Japan (DDBJ) (retrieved from the internet:<http://www.ddbj.nig.ac.j>). As a result, the sequence indicated with SEQ ID NOs. 2, 4, 6, 8, 10, 12 and 14 were demonstrated to form a family with eucaryotic or bacterial DMAPP:tRNA isopentenyl transferase or isopentenyl transferase involved in cytokinin synthesis of plant pathogens such as *Agrobacterium* that form gall. Moreover, the amino acid sequences indicated in SEQ ID NOs. 2, 10, 12 and 14 formed a single subgroup. Those genes that were related to this subgroup consisted of AAL83819 (DDBJ accession no.) of petunia origin and BAB86364 (DDBJ accession no.) of rice origin. In addition, the amino acid sequences indicated in SEQ ID NOs. 4, 6 and 8 also formed a single subgroup, and AW720363 (DDBJ accession no.) of bird's-foot trefoil *Lotus japonicus* origin was positioned in this subgroup.

Example 2

Excessive Expression in Plants of Genes Encoding Proteins Involved in Cytokinin Synthesis i) Production of Gene Insertion Vector for Plants pBI35T (WO 01/16332) was treated with EcoRI and HindIII to obtain a DNA fragment containing a promoter of cauliflower mosaic virus 35S RNA gene, a multi-cloning site and the terminator of 35S RNA gene. This was then treated with HindIII and EcoRI of pGPTV-KAN (Becker, R., et al., Plant Molecular Biology, 20, 1195-1197, 1992), and among the two fragments formed, the longer fragment was ligated to obtain pTK015 (FIG. 1). Similarly, this DNA fragment containing a promoter of cauliflower mosaic virus 35S RNA gene, a multi-cloning site and the terminator of 35S RNA gene was then treated with HindIII and EcoRI of pGPTV-Bar (Becker, R., et al., Plant Molecular Biology, 20, 1195-1197, 1992), and among the two fragments formed, the longer fragment was ligated to obtain pTK016.

For the predicted open reading frame of AF109376, DNA was amplified by incubating at 94° C. for 2 minutes followed by 40 cycles consisting of 15 seconds at 94° C., 30 seconds at 53° C. and 2 minutes and 40 seconds at 68° C. using the cDNA library of *Arabidopsis thaliana* for the template DNA of the PCR reaction, primer 398 (5'-TCCCCCGGGCGATGAT-GATGTTAAACCCTAGC-3') (SEQ ID NO. 15) and primer 399 (5'-TCCCCCGGGTC AATTTACTTCTGCTTCT-TGAACTTC) (SEQ ID NO. 16) as primers and pfx DNA polymerase (Gibco BRL), and purifying the amplified DNA followed by treatment with SmaI and repeated purification of the DNA. This was then cloned to the SmaI site of pTK015, after which the cloned product in the sense direction downstream from the 35S RNA gene promoter (35S promoter) of cauliflower mosaic virus was selected and designated as pTK015-AF109376.

AtIPT4 was amplified by incubating at 94° C. for 2 minutes followed by 42 cycles consisting of 15 seconds at 94° C., 20 seconds at 53° C. and 1 minute at 68° C. using the genomic DNA of *Arabidopsis thaliana* for the template of the PCR reaction, primer 421 (AAAATGAAGTGTAATGA-CAAAATGGTTGTG-3') (SEQ ID NO. 17) and primer 407 (5'-GTCCAAACTAGTTAAGACTTAAAAATC-3') (SEQ ID NO. 18) as primers and pfx DNA polymerase (Gibco BRL), followed by purification and cloning to the SmaI site of pTK015. The cloned product in the sense direction downstream from the 35S promoter was designated as pTK015-AtIPT4.

For AtIPT3, DNA was amplified using genomic DNA of *Arabidopsis thaliana* for the template, primer 703 (5'-CAC-CAGCAAGTTTATATTGCAAAGCGT-3') (SEQ ID NO. 19) and primer 705 (5'-GTTGTAACCACGTAAAA-GATAAGGGTG-3') (SEQ ID NO. 20) as primers and Herculase (trade name, Stratagene) as heat-resistant DNA synthase. The PCR reaction was carried out for 1 minute at 92° C. followed by 35 cycles consisting of 30 seconds at 92° C., 30 seconds at 55° C. and 2 minutes and 30 seconds at 70° C. Following purification of this product, it was cloned at the blunt terminal to the SmaI site of pTK016, and the cloned product of AtIPT3 in the sense direction downstream from the 35S promoter was selected and designated as pTK016-AtIPT3.

For pTK015, after digesting with SmaI and KpnI, the DNA was purified using the QUIAquick PCR Purification Kit (Qiagen). Here, the sequence of the multi-cloning site was altered by cloning primer 852(5'-CTCGAGTTGGCGCGC-CACCCGGGATTAATTAAGAC TAGTGGGGTAC-3') (SEQ ID NO. 27) and primer 853 (5'-CCCACTAGTCT-TAATTAA TCCCGGGTGGCGCGCCAACTCGAG-3') (SEQ ID NO. 28). Here, since primer 852 and primer 853 are synthetic DNA having mutually complementary sequences, this procedure was carried out by incubating the three elements consisting of a fragment obtained by digesting pTK015 with SmaI and KpnI, primer 852 and primer 853 in the presence of ligase under ordinary conditions. The plasmid produced in this manner was designated as pHM4. The only difference between pHM4 and pTK015 is the sequence of the multi-cloning site. Those unique sites present in the multi-cloning site of pTK015 consist of XbaI, XhoI, SmaI, PacI, SpeI, KpnI and SalI.

4 μg of pHM4 were digested with 20 units of BamHI. The terminals were blunted by incubating half the amount for 30 minutes at 70° C. in the presence of 200 μM deoxyATP, deoxyTTP, deoxyCTP, deoxyGTP and 1 unit of pfu DNA polymerase (Stratagene). After treating this for 1 hour at 37° C. with 20 units of calf intestine alkaline phosphatase (Takara), the DNA was purified using the QUIAquick PCR Purification Kit (Qiagen). Here, the cloned DNA fragment that was amplified (for 35 cycles consisting of 20 seconds at 94° C., 30 seconds at 55° C. and 1 minute at 72° C.) from genomic DNA of *Arabidopsis thaliana* using Herculase heat-resistant DNA polymerase (Stratagene), primer 918 (5'-ATG ACA GAA CTC AAC TTC CAC CT-3') (SEQ ID NO. 29)

and primer 879 (5'-CAAAAAAAAGATCTAATTTTGCAC-CAAATGCCGCTT-3') (SEQ ID NO. 30) was cloned and designated as pHM4-AtIPT1.

A cloned DNA fragment amplified from the genomic DNA of *Arabidopsis thaliana* using primer 533 (5'-ATTATG-CAAAATCTTACG TCCACATTCGTC-3') (SEQ ID NO. 31) and primer 881 (5'-ACAGGATCCTCA-CACTTTGTCTTTCACCAAG-3') (SEQ ID NO. 32) was cloned in the same manner as the production of pHM4-AtIPT1 and designated as pHM4-AtIPT8.

A sequence containing the entire code region of SEQ ID NO. 6 starting 66 bps upstream from the translation starting point ATG described in SEQ ID NO. 5 was amplified by PCR using genomic DNA extracted from a Columbia wild strain (Takara Shuzo) as a template and using primer 856 (5'-CCGCTCGAGA TGAAGCCATGCATGACGGCTC-3') (SEQ ID NO. 33) and primer 857 (5'-GGACTAGTCAC-CGGGAAATCGCCGCCA-3') (SEQ ID NO. 34). These primers contain restriction enzyme sites and were treated with XhoI and SpeI following PCR. This DNA fragment was cloned to pHM4, a vector excessive expression in plants, and designated as pHM4-AtIPT5.

ii) Gene Insertion into Plants pTK015, pTK015-AF109376, pTK015-AtIPT4 and pTK016-AtIPT3 were inserted into the callus of *Arabidopsis thaliana* using *Agrobacterium*. The method for inserting genes using *Agrobacterium* was in accordance with the method of Akama, et al. (Akama, K. et al., 1992 Plant Cell Rep., 12, 7-11). The calli containing the inserted genes were cultured in two types of media consisting of cytokinin-free medium [GM medium (Akama, K. et al., 1992 Plant Cell Rep., 12, 7-11) containing 50 μg/ml of kanamycin sulfate, 100 μg/ml of cefotaxime, 100 μg/ml of vancomycin and 0.3 μg/ml of indole acetate] and cytokinin-containing medium (cytokinin-free medium containing 0.5 μg/ml of trans-zeatin). When observed two weeks later, neither the calli transformed with pTK015 or calli transformed with pTK015-AF109376 formed shoots in the cytokinin-free medium, and only formed shoots in the cytokinin-containing medium. In contrast, the calli transformed with pTK015-AtIPT4 formed shoots in both the cytokinin-free and cytokinin-containing medium. In addition, calli transformed with pTK016-AtIPT3 similarly formed shoots in both the cytokinin-free and cytokinin-containing media.

In addition, calli of *Arabidopsis thaliana* respectively inserted with pHM4, pHM4-AtIPT1, pHM4-AtIPT8 and pHMR-AtIPT5 were cultured in cytokinin-free medium containing 0.2 μg/ml of indole acetate, 50 μg/ml of kanamycin and 100 μg/ml of claforan. The procedure was the same as the example in which AtIPT4 was inserted into calli. Although the calli containing pHM4 did not form shoots, the calli containing pHM4-AtIPT1, pHM4-AtIPT8 and pHM4-AtIPT5 formed shoot tissue.

On the basis of these findings, AtIPT4 and AtIPT3 were suggested to have the ability to induce shoots and the ability to synthesis cytokinins.

Figure 2:
FIG. 2 is a photograph of a plant body regenerated from *Arabidopsis thaliana* transformed by pHM4-AtIPT5.

In addition, it was also indicated that excessive expression of AtIPT1, AtIPT5 and AtIPT3 is capable of causing a cytokinin response.

iii) Excessive Expression of pHM4-AtIPT5 in Plants pHM4-AtIPT5 was transformed in *Arabidopsis thaliana* using the vacuum infiltration *Agrobacterium* infection method (O. Araki, Shujunsha Publishing, Cell Engineering Supplement, Plant Cell Engineering Series 4, Experimental Protocols in Model Plants, p. 109-113). The resulting seeds were cultivated in MS agar medium containing 50 μg/ml of kanamycin followed by selection of transformants. When the transformants were cultivated in vermiculite containing one-half the concentration of MS medium, an extremely large number of lateral buds were formed in several of the plants (causing the plants to appear bushy) (FIG. 2). This phenotype was not observed in pHM4 transformants cultivated as a control. As a result, it was determined that when AtIPT5 is expressed in excess, terminal bud dominance diminishes and lateral bud formation is promoted.

Example 3

Measurement of Enzyme Activity of Proteins Involved in Cytokinin Synthesis i) Plasmid Production for Measuring Enzyme Activity The code region was amplified by using the pTK015-AtIPT4 produced in Example 2 as a template, using primer 480 (5'-GGAATTCCATATGAAGTGTAATGA-CAAAATGGTTGA^3') (SEQ ID NO. 21) and primer 481 (5'-GAAGATCTGTCCAAACTAGTTAAGACTTAAAAA TC-3') (SEQ ID NO. 22) as primers, and using LA taq (Takara Shuzo). After purifying the amplified region, it was treated with NdeI and BglII followed by again purifying the DNA. This DNA fragment was cloned between the NdeI and BamHI sites of pET16b (Novagen) to produce pET16b-AtIPT4.

In addition, the coding region was amplified using pTK015-AF109376 as the template for the PCR reaction, using primer 550 (5'-GATCCCCGGCATATGATGATGT-TAAACCCTAGC-3') (SEQ ID NO. 23) and primer 551 (5'-ACGGTACCCATA TGTCAATTTACTTCTGCTTCT-TGAAC-3') (SEQ ID NO. 24) as primers, and using Herculase (Stratagene) as heat-resistant DNA polymerase. This was then treated with NdeI and cloned to the NdeI site of pET16b to produce pET16b-AF109376.

Moreover, the coding region was amplified using genomic DNA of *Arabidopsis thaliana* as the template for the PCR reaction, using primer 741 (5'-TTATACATATGAAGCCAT-GCATGACGGCTCTAAG-3') (SEQ ID NO. 25) and primer 742 (5'-CGGGATCCTCACCGGG AAATCGCCGCCA-3') (SEQ ID NO. 26) as primers, and using LA taq (Takara Shuzo) as heat-resistant enzyme. Following purification, the DNA was treated with NdeI and BamHI and cloned between the NdeI and BamHI sites of pET15b (Novagen) to produce pET15b-AtIPT5.

ii) Measurement of Enzyme Activity of *E. Coli* Extract

As was previously described, AtIPT1, AtIPT4, AtIPT8 and AtIPT6 form a single subgroup, while AtIPT3, AtIPT5 and AtIPT7 form a different subgroup. Enzyme activity in *E. coli* was measured from each for a single gene.

After culturing *E. coli* strain AD494(DE3)pLysS containing pET16b-AtIPT4, pET16b-AF109376 or pET15b-AtIPT5 for 12 hours at 20° C. in the presence of 1 mM IPTG, the microorganisms were collected by centrifugation, and after adding Buffer A (25 mM Tris-HCl, 50 mM KCl, 5 mM β-mercaptoethanol, 1 mM PMSF and 20 μg/ml of leupeptin) to an OD600 of 100, the *E. coli* were disrupted by freezing and thawing. The disrupted *E. coli* were then centrifuged for 10 minutes at 300000 g followed by recovery of the supernatants. 10 μl of these supernatants were mixed with Buffer A containing 60 μM DMAPP, 5 μM [3H]AMP (722 GBq/mmol) and 10 mM $MgCl_2$ followed by incubation for 30 minutes at 25° C. Subsequently, 50 mM of Tris-HCl (pH 9) was added to this reaction liquid followed by the addition of calf intestine alkaline phosphatase to a concentration of 2 units/30 μl and incubating for 30 minutes at 37° C. to carry out a dephosphatization reaction. As a result of developing the reaction liquid by C18 reversed-phase thin layer chromatography (mobile phase: 50% methanol) and detecting the reaction products by autoradiography, formation of isopentenyl adenosine was confirmed in the reaction liquids containing extracts of *E. coli* having pET16b-AtIPT4 and pET15b-AtIPT5. However, formation activity of isopentenyl adenosine was not observed in the extract of *E. coli* containing pET16b-AF109376.

iii) Measurement of Enzyme Activity of Purified Proteins

Similar to Example 3, Part (i), AtIPT4 was cloned in pET32b (Novagen) and an extract was prepared from *E. coli* in the same manner as Example 3, Part (ii). This was designated as Sample A. 400 μl of Ni-NTA agarose suspension (containing 110 μl of Ni-NTA agarose as precipitate, 30 mM $NaH_2PO_4$ (pH 8), 15 mM indazole, 0.9 M NaCl, 7.5 mM β-mercaptoethanol, 0.5 mM PMSF and 30 μg/ml of leupeptin) were added to 800 μl of Sample A. This suspension was designated as Sample B. Sample B was then centrifuged to separate into supernatant (Sample C) and precipitate. Washing liquid (consisting of 20 mM $NaH_2PO_4$ (pH 8), 10 mM indazole, 0.3 M NaCl, 5 mM β-mercaptoethanol, 0.5 mM PMSF and 10 μg/ml of leupeptin) was added to the precipitate, and the Ni-NTA agarose was washed four times using a procedure in which the precipitate was recovered by centrifugation. This Ni-NTA agarose was then suspended in 500 μl of washing liquid and designated as Sample D. 50 μl of Sample D were then mixed with 50 μl of 2× reaction liquid (25 mM Tris-HCl (pH 7.5), 75 mM KCl, 10 mM $MgCl_2$, 10 μg/ml of leupeptin, 1 mM PMSF and 66 μM DMAPP) containing one of the nucleotides of ATP, ADP or AMP or adenosine or adenine at 0.25 μM, which were labeled with $^3H$, and allowed to react for 30 minutes at 23° C. After adding 700 μl of ethyl acetate to this reaction liquid followed by stirring and centrifuging, 550 μl of the ethyl acetate layer were recovered followed by the addition of 500 μl of distilled water. After stirring and centrifugal separation, 350 μl of the ethyl acetate layer were recovered followed again by the addition of 500 μl of distilled water. After again stirring and separating by centrifugation, 0.5 ml of ACSII (Pharmacia) were added to 50 μl of the ethyl acetate layer followed by measurement of radioactivity with a liquid scintillation counter. As a result, the dimethylallyl group of DMAPP was found to have efficiently transferred to ATP and ADP. Thus, it was shown that the AtIPT4 product has activity that transfers a dimethylallyl group to ATP and ADP.

When the Km for ATP was measured in the presence of 0.4 mM DMAPP using purified recombinant AtIPT4 protein (2 ng/ml), the resulting value was comparable to the Km of 11.1 μM (Morris, et al., Aust. J. Plant Physiol., 20, 621-637, 1993) of tzs for AMP. In addition, when the Km for DMAPP was measured in the presence of 200 μM ATP, the value was 6.5 μM.

Similarly, AtIPT1 also encoded protein having activity that transfers a dimethylallyl group to ATP and ADP.

iv) Identification of Reaction Products

The aforementioned Sample D was mixed with an equal volume of 2× reaction liquid (containing 1 mM ATP and 1 mM DMAPP) and allowed to react for 1 hour at 25° C. After centrifuging, the supernatant was divided into two equal portions, and one of the portions was treated with calf intestine alkaline phosphatase in the same manner as previously described. After diluting each portion with 3 volumes of acetone and holding for 30 minutes at −80° C., they were centrifuged for 30 minutes at 17,000×g to remove the protein. After drying the supernatant to a solid under reduced pressure, it was dissolved in methanol. A portion of the dried supernatant was fractionated with the Chemocobond ODS-W column (Chemco). Elution was carried out using a linear concentration gradient by first eluting for 15 minutes with 20 mM $KH_2PO_4$ followed by 30 minutes with an 80% aqueous acetonitrile solution containing $K_2HPO_4$ ranging from 20 mM to 4 mM. The sample not treated with calf intestine alkaline phosphatase exhibited two main peaks in Chemocobond ODS-W column chromatography. The retention time of the peak that eluted first coincided with the retention time of ATP. The retention time of the peak (Peak A) that eluted later did not coincide with any of the retention times of ATP, adenosine or isopentenyl adenosine. The sample treated with calf intestine alkaline phosphatase also exhibited two main peaks in Chemocobond ODS-W column chromatography. The retention time of the peak that eluted first coincided with the retention time of adenosine, while the retention time of the peak that eluted later (Peak B) coincided with that of isopentenyl adenosine.

After drying the fractions of Peaks A and B, they were dissolved in ethanol and analyzed by fast atom bombardment mass spectrometry (JMS-SX102 or JEOL Mstation, JOEL Datum Ltd.). As a result, a signal originating in the compound of Peak A was unable to be obtained, because of inhibition of ionization by the triphosphate group. Signals originating in the compound of Peak B were observed at m/z values of 336 and 204, with the former corresponding to isopentenyl adenosine, and the latter corresponding to a decomposition product of isopentenyl adenosine. On the basis of the above, Peak A was thought to be isopentenyl ATP (also referred to as iPTP), which is a compound resulting from the phosphatization of isopentenyl adenosine.

When the genes indicated with SEQ ID NOs. 2 and 6 were expressed in *E. coli*, both exhibited cytokinin synthesis activity. In addition, a cytokinin response was evoked in the case of excessive expression in plants of enzymes of the genes indicated in SEQ ID NOs. 2, 4, 6, 10 and 12. In addition, SEQ ID NOs. 2, 10, 12 and 14 or SEQ ID NOs. 4, 6 and 8 were clearly shown to be extremely closely related in terms of their respective molecular systems. Thus, each of these are considered to be cytokinin synthesis enzymes. Thus, it was possible to control cell division, differentiation, axillary bud length, regulation of nutrient distribution, inhibition of aging, reproductive growth and seed growth by controlling the expression of the genes of the present invention and their analogous genes. In addition, since they are plant genes, the appearance of toxicity and so forth of proteins expressed in plants into which these genes have been inserted is unlikely.

Since ATP can be efficiently used as a substrate of cytokinin synthesis, these genes are expected to function more effectively in plants than cytokinin synthesis genes originating in bacteria using AMP as substrate.

EXPLANATION OF SYMBOLS

PAg7:TERMINATOR OF T-DNA GENE 7
NPTII:NEOMYCIN PHOSPHOTRANSFERASE II
PNOS:NOPALINE SYNTHETASE PROMOTER
P35S:PROMOTER OF CAULIFLOWER MOSAIC VIRUS 35S RNA GENE
PA35S:TERMINATOR OF CAULIFLOWER MOSAIC VIRUS 35S RNA GENE
LB:LEFT BORDER OF T-DNA
RB:RIGHT BORDER OF T-DNA

The invention claimed is:

1. An isolated polynucleotide consisting of a nucleotide sequence encoding a protein having cytokinin synthesis activity and the amino acid sequence of SEQ ID NO: 6, or an isolated polynucleotide only encoding a protein having cytokinin synthesis activity and the amino acid sequence of SEQ ID NO: 6.

2. An isolated polynucleotide consisting of a nucleotide sequence encoding a protein having cytokinin synthesis activity wherein the protein has a modified amino acid sequence resulting from the addition, deletion, or substitution of one to 25 amino acids in SEQ ID NO:6 or an isolated nucleotide sequence only encoding a protein having cytokinin synthesis activity, wherein the protein has a modified amino acid sequence resulting from the addition, deletion, or substitution of one to 25 amino acids in SEQ ID NO:6.

3. A vector comprising the isolated polynucleotide of claim 1 or claim 2.

4. An isolated host cell transformed with the vector of claim 3.

5. The transformed host cell of claim 4, wherein the transformed host cell is a plant cell.

6. A plant cell into which the polynucleotide of claim 3 has been inserted.

7. A method for regulating the growth of a plant or plant cells by inserting the polynucleotide of claim 1 into a plant cell and expressing said polynucleotide to regulate the growth of the plant cells.

8. A method for inducing adventitious bud formation in a plant or plant cells by inserting the polynucleotide of claim 1 into a plant cell, and expressing the polynucleotide to induce adventitious bud formation in the plant cells.

9. A method for regulating the growth of a plant or plant cells by inserting the polynucleotide of claim 2 into a plant cell and expressing the polynucleotide to regulate the growth of the plant cells.

10. A method for inducing adventitious bud formation in a plant or plant cells by inserting the polynucleotide of claim 2 into a plant cell, and expressing the polynucleotide to induce adventitious bud formation in the plant cells.

* * * * *

SEQUENCE LISTING

<160> NUMBER OF SEQ ID NOS: 35

<210> SEQ ID NO 1
<211> LENGTH: 957
<212> TYPE: DNA
<213> ORGANISM: Arabidopsis thaliana
<220> FEATURE:
<221> NAME/KEY: CDS
<222> LOCATION: (1)..(954)

<400> SEQUENCE: 1

```
atg aag tgt aat gac aaa atg gtt gtg atc atg ggt gcc acc ggt tct      48
Met Lys Cys Asn Asp Lys Met Val Val Ile Met Gly Ala Thr Gly Ser
 1               5                  10                  15 ggc aag tca tca ctc tct gtt gat ctc gct tta cat ttt aaa gcc gag      96
Gly Lys Ser Ser Leu Ser Val Asp Leu Ala Leu His Phe Lys Ala Glu
                20                  25                  30 atc atc aac tct gac aaa atg cag ttc tac gat ggc ttg aag atc acc     144
Ile Ile Asn Ser Asp Lys Met Gln Phe Tyr Asp Gly Leu Lys Ile Thr
            35                  40                  45 acg aat caa tcg acc att gaa gat cga cgt gga gtg cca cat cac ctt     192
Thr Asn Gln Ser Thr Ile Glu Asp Arg Arg Gly Val Pro His His Leu
        50                  55                  60 ctc ggt gaa cta aac ccg gag gct gga gaa gtc aca gcg gca gaa ttt     240
Leu Gly Glu Leu Asn Pro Glu Ala Gly Glu Val Thr Ala Ala Glu Phe
 65                  70                  75                  80 cgc gtt atg gcg gct gaa gcc atc tcc gag att act caa cgt aaa aag     288
Arg Val Met Ala Ala Glu Ala Ile Ser Glu Ile Thr Gln Arg Lys Lys
                 85                  90                  95 ctc cca atc ctt gcc ggt gga tcc aac tca tac att cat gct ctc ctt     336
Leu Pro Ile Leu Ala Gly Gly Ser Asn Ser Tyr Ile His Ala Leu Leu
                100                 105                 110 gca aaa tct tat gac cct gaa aac tat ccg ttt tct gat cac aag ggc     384
Ala Lys Ser Tyr Asp Pro Glu Asn Tyr Pro Phe Ser Asp His Lys Gly
            115                 120                 125 tca atc tgc tcc gag ttg aaa tat gat tgt tgt ttc att tgg ata gat     432
Ser Ile Cys Ser Glu Leu Lys Tyr Asp Cys Cys Phe Ile Trp Ile Asp
        130                 135                 140 gtg gat cag tct gtg tta ttc gag tat ctt tct tta cgt ttg gat ctt     480
Val Asp Gln Ser Val Leu Phe Glu Tyr Leu Ser Leu Arg Leu Asp Leu
145                 150                 155                 160 atg atg aag tca ggt atg ttc gag gag atc gct gag ttc cac cgc tct     528
Met Met Lys Ser Gly Met Phe Glu Glu Ile Ala Glu Phe His Arg Ser
                165                 170                 175 aag aag gcc ccg aaa gag cca ttg ggg ata tgg aag gct ata gga gtg     576
Lys Lys Ala Pro Lys Glu Pro Leu Gly Ile Trp Lys Ala Ile Gly Val
            180                 185                 190 caa gag ttt gat gac tac ctc aaa atg tac aag tgg gac aat gac atg     624
Gln Glu Phe Asp Asp Tyr Leu Lys Met Tyr Lys Trp Asp Asn Asp Met
        195                 200                 205 gat aaa tgg gac cct atg aga aag gag gct tat gag aag gcg gtg aga     672
Asp Lys Trp Asp Pro Met Arg Lys Glu Ala Tyr Glu Lys Ala Val Arg
    210                 215                 220 gcc atc aaa gaa aac aca ttt cag ctc aca aag gat caa atc acg aag     720
Ala Ile Lys Glu Asn Thr Phe Gln Leu Thr Lys Asp Gln Ile Thr Lys
225                 230                 235                 240 atc aac aag ctg aga aat gcc ggg tgg gac ata aag aag gtg gat gct     768
Ile Asn Lys Leu Arg Asn Ala Gly Trp Asp Ile Lys Lys Val Asp Ala
                245                 250                 255
```

```
aca gca tcg ttt cga gag gca att agg gca gcc aag gaa ggc gaa ggt    816
Thr Ala Ser Phe Arg Glu Ala Ile Arg Ala Ala Lys Glu Gly Glu Gly
        260                 265                 270 gta gcc gag atg cag aga aag ata tgg aac aag gaa gtg ttg gaa ccg    864
Val Ala Glu Met Gln Arg Lys Ile Trp Asn Lys Glu Val Leu Glu Pro
    275                 280                 285 tgt gtg aag att gtc agg agc cac ttg gac caa ccg atc aac tat tat    912
Cys Val Lys Ile Val Arg Ser His Leu Asp Gln Pro Ile Asn Tyr Tyr
290                 295                 300 tat tat tac ttt tat tta cta aaa aga ttt tta agt ctt aac tag        957
Tyr Tyr Tyr Phe Tyr Leu Leu Lys Arg Phe Leu Ser Leu Asn
305                 310                 315

<210> SEQ ID NO 2
<211> LENGTH: 318
<212> TYPE: PRT
<213> ORGANISM: Arabidopsis thaliana

<400> SEQUENCE: 2

Met Lys Cys Asn Asp Lys Met Val Val Ile Met Gly Ala Thr Gly Ser
1               5                   10                  15

Gly Lys Ser Ser Leu Ser Val Asp Leu Ala Leu His Phe Lys Ala Glu
            20                  25                  30

Ile Ile Asn Ser Asp Lys Met Gln Phe Tyr Asp Gly Leu Lys Ile Thr
        35                  40                  45

Thr Asn Gln Ser Thr Ile Glu Asp Arg Arg Gly Val Pro His His Leu
    50                  55                  60

Leu Gly Glu Leu Asn Pro Glu Ala Gly Glu Val Thr Ala Ala Glu Phe
65                  70                  75                  80

Arg Val Met Ala Ala Glu Ala Ile Ser Glu Ile Thr Gln Arg Lys Lys
                85                  90                  95

Leu Pro Ile Leu Ala Gly Gly Ser Asn Ser Tyr Ile His Ala Leu Leu
            100                 105                 110

Ala Lys Ser Tyr Asp Pro Glu Asn Tyr Pro Phe Ser Asp His Lys Gly
        115                 120                 125

Ser Ile Cys Ser Glu Leu Lys Tyr Asp Cys Cys Phe Ile Trp Ile Asp
    130                 135                 140

Val Asp Gln Ser Val Leu Phe Glu Tyr Leu Ser Leu Arg Leu Asp Leu
145                 150                 155                 160

Met Met Lys Ser Gly Met Phe Glu Glu Ile Ala Glu Phe His Arg Ser
                165                 170                 175

Lys Lys Ala Pro Lys Glu Pro Leu Gly Ile Trp Lys Ala Ile Gly Val
            180                 185                 190

Gln Glu Phe Asp Asp Tyr Leu Lys Met Tyr Lys Trp Asp Asn Asp Met
        195                 200                 205

Asp Lys Trp Asp Pro Met Arg Lys Glu Ala Tyr Glu Lys Ala Val Arg
    210                 215                 220

Ala Ile Lys Glu Asn Thr Phe Gln Leu Thr Lys Asp Gln Ile Thr Lys
225                 230                 235                 240

Ile Asn Lys Leu Arg Asn Ala Gly Trp Asp Ile Lys Lys Val Asp Ala
                245                 250                 255

Thr Ala Ser Phe Arg Glu Ala Ile Arg Ala Ala Lys Glu Gly Glu Gly
            260                 265                 270

Val Ala Glu Met Gln Arg Lys Ile Trp Asn Lys Glu Val Leu Glu Pro
        275                 280                 285

Cys Val Lys Ile Val Arg Ser His Leu Asp Gln Pro Ile Asn Tyr Tyr
```

-continued

```
                  290                 295                 300
Tyr Tyr Tyr Phe Tyr Leu Leu Lys Arg Phe Leu Ser Leu Asn
305                 310                 315

<210> SEQ ID NO 3
<211> LENGTH: 1011
<212> TYPE: DNA
<213> ORGANISM: Arabidopsis thaliana
<220> FEATURE:
<221> NAME/KEY: CDS
<222> LOCATION: (1)..(1008)

<400> SEQUENCE: 3 atg atc atg aag ata tct atg gct atg tgc aaa caa cca ttg cct cct       48
Met Ile Met Lys Ile Ser Met Ala Met Cys Lys Gln Pro Leu Pro Pro
  1               5                  10                  15 tcg ccg act tta gac ttc cct cca gcg aga ttt ggt ccc aat atg cta       96
Ser Pro Thr Leu Asp Phe Pro Pro Ala Arg Phe Gly Pro Asn Met Leu
             20                  25                  30 act cta aac cca tac ggt cca aag gac aaa gtt gtg gtc atc atg ggt      144
Thr Leu Asn Pro Tyr Gly Pro Lys Asp Lys Val Val Val Ile Met Gly
         35                  40                  45 gct acc ggg aca ggc aag tca cga ctc tcc gtg gat ata gcc aca cgt      192
Ala Thr Gly Thr Gly Lys Ser Arg Leu Ser Val Asp Ile Ala Thr Arg
     50                  55                  60 ttt cgg gct gag atc ata aac tca gac aag ata caa gtc cac caa ggt      240
Phe Arg Ala Glu Ile Ile Asn Ser Asp Lys Ile Gln Val His Gln Gly
 65                  70                  75                  80 cta gac att gta acc aac aag atc acg agc gag gag agc tgc ggg gta      288
Leu Asp Ile Val Thr Asn Lys Ile Thr Ser Glu Glu Ser Cys Gly Val
                 85                  90                  95 ccg cac cat ctc ctc ggc gtc ttg ccg cct gaa gcc gac tta acc gcc      336
Pro His His Leu Leu Gly Val Leu Pro Pro Glu Ala Asp Leu Thr Ala
            100                 105                 110 gcg aat tac tgt cac atg gcg aat ctc tcc att gaa tcc gtc cta aac      384
Ala Asn Tyr Cys His Met Ala Asn Leu Ser Ile Glu Ser Val Leu Asn
        115                 120                 125 cgt gga aag ctt cca atc atc gtt gga ggt tcc aac tct tac gtg gag      432
Arg Gly Lys Leu Pro Ile Ile Val Gly Gly Ser Asn Ser Tyr Val Glu
    130                 135                 140 gct cta gtg gat gac aaa gaa aac aag ttc agg tcg aga tac gac tgt      480
Ala Leu Val Asp Asp Lys Glu Asn Lys Phe Arg Ser Arg Tyr Asp Cys
145                 150                 155                 160 tgt ttt cta tgg gtg gac gtg gca ctt ccc gtt ttg cac ggg ttc gtg      528
Cys Phe Leu Trp Val Asp Val Ala Leu Pro Val Leu His Gly Phe Val
                165                 170                 175 tct gag aga gtt gac aag atg gtg gag agt gga atg gtt gag gaa gtc      576
Ser Glu Arg Val Asp Lys Met Val Glu Ser Gly Met Val Glu Glu Val
            180                 185                 190 aga gaa ttt ttc gac ttt tcg aac tct gat tac tca aga ggg atc aag      624
Arg Glu Phe Phe Asp Phe Ser Asn Ser Asp Tyr Ser Arg Gly Ile Lys
        195                 200                 205 aaa gca atc gga ttt ccg gag ttt gac agg ttt ttc agg aac gag cag      672
Lys Ala Ile Gly Phe Pro Glu Phe Asp Arg Phe Phe Arg Asn Glu Gln
    210                 215                 220 ttc ttg aat gtg gaa gac aga gaa gaa ctg tta agt aaa gtg ttg gaa      720
Phe Leu Asn Val Glu Asp Arg Glu Glu Leu Leu Ser Lys Val Leu Glu
225                 230                 235                 240 gaa ata aag agg aat aca ttt gag tta gct tgt agg cag aga gaa aag      768
Glu Ile Lys Arg Asn Thr Phe Glu Leu Ala Cys Arg Gln Arg Glu Lys
                245                 250                 255
```

```
atc gaa cgg ttg aga aaa gtg aag aag tgg tct att cag aga gtg gat    816
Ile Glu Arg Leu Arg Lys Val Lys Lys Trp Ser Ile Gln Arg Val Asp
        260                 265                 270 gcg act cca gtc ttt aca aag cga agg tcc aag atg gat gct aac gtg    864
Ala Thr Pro Val Phe Thr Lys Arg Arg Ser Lys Met Asp Ala Asn Val
        275                 280                 285 gcc tgg gag agg ctc gtg gct gga cca agc aca gat act gtg tcg cgg    912
Ala Trp Glu Arg Leu Val Ala Gly Pro Ser Thr Asp Thr Val Ser Arg
        290                 295                 300 ttt ctg ctg gac att gcc agc cga cga ccg ctc gtg gaa gct tca aca    960
Phe Leu Leu Asp Ile Ala Ser Arg Arg Pro Leu Val Glu Ala Ser Thr
305                 310                 315                 320 gcg gtt gcg gcc gcc atg gaa cgc gag ttg tcg cgg tgt cta gtg gcg   1008
Ala Val Ala Ala Ala Met Glu Arg Glu Leu Ser Arg Cys Leu Val Ala
                325                 330                 335 tga                                                                1011
```

<210> SEQ ID NO 4
<211> LENGTH: 336
<212> TYPE: PRT
<213> ORGANISM: Arabidopsis thaliana

<400> SEQUENCE: 4

```
Met Ile Met Lys Ile Ser Met Ala Met Cys Lys Gln Pro Leu Pro Pro
 1               5                  10                  15

Ser Pro Thr Leu Asp Phe Pro Pro Ala Arg Phe Gly Pro Asn Met Leu
            20                  25                  30

Thr Leu Asn Pro Tyr Gly Pro Lys Asp Lys Val Val Ile Met Gly
        35                  40                  45

Ala Thr Gly Thr Gly Lys Ser Arg Leu Ser Val Asp Ile Ala Thr Arg
    50                  55                  60

Phe Arg Ala Glu Ile Ile Asn Ser Asp Lys Ile Gln Val His Gln Gly
65                  70                  75                  80

Leu Asp Ile Val Thr Asn Lys Ile Thr Ser Glu Glu Ser Cys Gly Val
                85                  90                  95

Pro His His Leu Leu Gly Val Leu Pro Pro Glu Ala Asp Leu Thr Ala
            100                 105                 110

Ala Asn Tyr Cys His Met Ala Asn Leu Ser Ile Glu Ser Val Leu Asn
        115                 120                 125

Arg Gly Lys Leu Pro Ile Ile Val Gly Gly Ser Asn Ser Tyr Val Glu
    130                 135                 140

Ala Leu Val Asp Asp Lys Glu Asn Lys Phe Arg Ser Arg Tyr Asp Cys
145                 150                 155                 160

Cys Phe Leu Trp Val Asp Val Ala Leu Pro Val Leu His Gly Phe Val
                165                 170                 175

Ser Glu Arg Val Asp Lys Met Val Glu Ser Gly Met Val Glu Glu Val
            180                 185                 190

Arg Glu Phe Phe Asp Phe Ser Asn Ser Asp Tyr Ser Arg Gly Ile Lys
        195                 200                 205

Lys Ala Ile Gly Phe Pro Glu Phe Asp Arg Phe Phe Arg Asn Glu Gln
    210                 215                 220

Phe Leu Asn Val Glu Asp Arg Glu Glu Leu Leu Ser Lys Val Leu Glu
225                 230                 235                 240

Glu Ile Lys Arg Asn Thr Phe Glu Leu Ala Cys Arg Gln Arg Glu Lys
                245                 250                 255
```

```
Ile Glu Arg Leu Arg Lys Val Lys Lys Trp Ser Ile Gln Arg Val Asp
            260                 265                 270

Ala Thr Pro Val Phe Thr Lys Arg Arg Ser Lys Met Asp Ala Asn Val
            275                 280                 285

Ala Trp Glu Arg Leu Val Ala Gly Pro Ser Thr Asp Thr Val Ser Arg
            290                 295                 300

Phe Leu Leu Asp Ile Ala Ser Arg Arg Pro Leu Val Glu Ala Ser Thr
305                 310                 315                 320

Ala Val Ala Ala Ala Met Glu Arg Glu Leu Ser Arg Cys Leu Val Ala
                325                 330                 335

<210> SEQ ID NO 5
<211> LENGTH: 990
<212> TYPE: DNA
<213> ORGANISM: Arabidopsis thaliana
<220> FEATURE:
<221> NAME/KEY: CDS
<222> LOCATION: (1)..(990)

<400> SEQUENCE: 5 atg aag cca tgc atg acg gct cta aga caa gtg att caa cca ttg tcg     48
Met Lys Pro Cys Met Thr Ala Leu Arg Gln Val Ile Gln Pro Leu Ser
 1               5                  10                  15 ttg aac ttc caa gga aac atg gtg gac gtt ccg ttt ttc cgg cga aaa     96
Leu Asn Phe Gln Gly Asn Met Val Asp Val Pro Phe Phe Arg Arg Lys
             20                  25                  30 gac aag gtt gtt ttc gtc atg gga gcc acc gga acc ggc aaa tct cgt    144
Asp Lys Val Val Phe Val Met Gly Ala Thr Gly Thr Gly Lys Ser Arg
         35                  40                  45 cta gcc att gac cta gcc act cgt ttt ccg gcg gag att gta aac tcc    192
Leu Ala Ile Asp Leu Ala Thr Arg Phe Pro Ala Glu Ile Val Asn Ser
     50                  55                  60 gac aag atc cag gtc tat aaa ggt cta gac att gtg act aac aaa gtc    240
Asp Lys Ile Gln Val Tyr Lys Gly Leu Asp Ile Val Thr Asn Lys Val
 65                  70                  75                  80 act cct gag gaa agc ctt ggc gtt cct cac cac ctt ctc ggc acc gtc    288
Thr Pro Glu Glu Ser Leu Gly Val Pro His His Leu Leu Gly Thr Val
                 85                  90                  95 cac gac act tac gaa gat ttc acg gcg gag gat ttt cag cgt gaa gca    336
His Asp Thr Tyr Glu Asp Phe Thr Ala Glu Asp Phe Gln Arg Glu Ala
            100                 105                 110 atc agg gcc gtc gag tca atc gtc cag aga gac cgt gtc ccg atc ata    384
Ile Arg Ala Val Glu Ser Ile Val Gln Arg Asp Arg Val Pro Ile Ile
        115                 120                 125 gcc ggt ggt tcc aat tct tac atc gag gct ctg gtc aac gat tgc gtt    432
Ala Gly Gly Ser Asn Ser Tyr Ile Glu Ala Leu Val Asn Asp Cys Val
    130                 135                 140 gac ttc cgg tta agg tat aat tgt tgc ttc ttg tgg gtc gac gtc tct    480
Asp Phe Arg Leu Arg Tyr Asn Cys Cys Phe Leu Trp Val Asp Val Ser
145                 150                 155                 160 aga ccg gtt tta cac tcg ttt gtc tcg gag cga gtt gat aag atg gtt    528
Arg Pro Val Leu His Ser Phe Val Ser Glu Arg Val Asp Lys Met Val
                165                 170                 175 gat atg ggt ctc gtc gac gag gtt cgc cgc atc ttc gat ccg tct tcg    576
Asp Met Gly Leu Val Asp Glu Val Arg Arg Ile Phe Asp Pro Ser Ser
            180                 185                 190 tcg gat tac tcc gct gga att cgc cga gcc att gga gtt cca gag ctc    624
Ser Asp Tyr Ser Ala Gly Ile Arg Arg Ala Ile Gly Val Pro Glu Leu
        195                 200                 205 gac gaa ttt ctc cgt tcg gag atg cgg aat tat ccg gcg gag acg acg    672
Asp Glu Phe Leu Arg Ser Glu Met Arg Asn Tyr Pro Ala Glu Thr Thr
```

-continued

```
Asp Glu Phe Leu Arg Ser Glu Met Arg Asn Tyr Pro Ala Glu Thr Thr
    210                 215                 220 gag aga ctt ctt gaa acg gcg atc gag aag att aaa gag aac act tgt      720
Glu Arg Leu Leu Glu Thr Ala Ile Glu Lys Ile Lys Glu Asn Thr Cys
225                 230                 235                 240 ttg ctt gcg tgt aga caa ttg cag aag att caa agg ctt tac aag cag      768
Leu Leu Ala Cys Arg Gln Leu Gln Lys Ile Gln Arg Leu Tyr Lys Gln
                245                 250                 255 tgg aag tgg aac atg cac cgt gtc gac gcg acg gag gtt ttt ctc cga      816
Trp Lys Trp Asn Met His Arg Val Asp Ala Thr Glu Val Phe Leu Arg
            260                 265                 270 cga gga gaa gaa gct gat gag gct tgg gat aac tca gtg gct cat ccg      864
Arg Gly Glu Glu Ala Asp Glu Ala Trp Asp Asn Ser Val Ala His Pro
        275                 280                 285 agc gca ctc gcc gtc gaa aag ttc ctt agt tac agc gat gac cac cat      912
Ser Ala Leu Ala Val Glu Lys Phe Leu Ser Tyr Ser Asp Asp His His
    290                 295                 300 ttg gaa ggc gcc aat att ctc cta ccg gag atc tct gcc gtt ccg cct      960
Leu Glu Gly Ala Asn Ile Leu Leu Pro Glu Ile Ser Ala Val Pro Pro
305                 310                 315                 320 ctt cca gcc gcc gtg gcg gcg att tcc cgg                              990
Leu Pro Ala Ala Val Ala Ala Ile Ser Arg
                325                 330

<210> SEQ ID NO 6
<211> LENGTH: 330
<212> TYPE: PRT
<213> ORGANISM: Arabidopsis thaliana

<400> SEQUENCE: 6

Met Lys Pro Cys Met Thr Ala Leu Arg Gln Val Ile Gln Pro Leu Ser
1               5                   10                  15

Leu Asn Phe Gln Gly Asn Met Val Asp Val Pro Phe Phe Arg Arg Lys
            20                  25                  30

Asp Lys Val Val Phe Val Met Gly Ala Thr Gly Thr Gly Lys Ser Arg
        35                  40                  45

Leu Ala Ile Asp Leu Ala Thr Arg Phe Pro Ala Glu Ile Val Asn Ser
    50                  55                  60

Asp Lys Ile Gln Val Tyr Lys Gly Leu Asp Ile Val Thr Asn Lys Val
65                  70                  75                  80

Thr Pro Glu Glu Ser Leu Gly Val Pro His His Leu Leu Gly Thr Val
                85                  90                  95

His Asp Thr Tyr Glu Asp Phe Thr Ala Glu Asp Phe Gln Arg Glu Ala
            100                 105                 110

Ile Arg Ala Val Glu Ser Ile Val Gln Arg Asp Arg Val Pro Ile Ile
        115                 120                 125

Ala Gly Gly Ser Asn Ser Tyr Ile Glu Ala Leu Val Asn Asp Cys Val
    130                 135                 140

Asp Phe Arg Leu Arg Tyr Asn Cys Cys Phe Leu Trp Val Asp Val Ser
145                 150                 155                 160

Arg Pro Val Leu His Ser Phe Val Ser Glu Arg Val Asp Lys Met Val
                165                 170                 175

Asp Met Gly Leu Val Asp Glu Val Arg Arg Ile Phe Asp Pro Ser Ser
            180                 185                 190

Ser Asp Tyr Ser Ala Gly Ile Arg Arg Ala Ile Gly Val Pro Glu Leu
        195                 200                 205

Asp Glu Phe Leu Arg Ser Glu Met Arg Asn Tyr Pro Ala Glu Thr Thr
```

-continued

```
                210                 215                 220
Glu Arg Leu Leu Glu Thr Ala Ile Glu Lys Ile Lys Glu Asn Thr Cys
225                 230                 235                 240

Leu Leu Ala Cys Arg Gln Leu Gln Lys Ile Gln Arg Leu Tyr Lys Gln
                245                 250                 255

Trp Lys Trp Asn Met His Arg Val Asp Ala Thr Glu Val Phe Leu Arg
            260                 265                 270

Arg Gly Glu Glu Ala Asp Glu Ala Trp Asp Asn Ser Val Ala His Pro
            275                 280                 285

Ser Ala Leu Ala Val Glu Lys Phe Leu Ser Tyr Ser Asp Asp His His
        290                 295                 300

Leu Glu Gly Ala Asn Ile Leu Leu Pro Glu Ile Ser Ala Val Pro Pro
305                 310                 315                 320

Leu Pro Ala Ala Val Ala Ala Ile Ser Arg
                325                 330

<210> SEQ ID NO 7
<211> LENGTH: 990
<212> TYPE: DNA
<213> ORGANISM: Arabidopsis thaliana
<220> FEATURE:
<221> NAME/KEY: CDS
<222> LOCATION: (1)..(987)

<400> SEQUENCE: 7
```

```
atg aag ttc tca atc tca tca ctg aag cag gta caa cca atc ttg tgc      48
Met Lys Phe Ser Ile Ser Ser Leu Lys Gln Val Gln Pro Ile Leu Cys
  1               5                  10                  15 ttc aag aac aag cta tct aag gtc aac gtc aac tct ttt ctc cat ccc      96
Phe Lys Asn Lys Leu Ser Lys Val Asn Val Asn Ser Phe Leu His Pro
             20                  25                  30 aaa gaa aaa gtc atc ttt gtg atg gga gct acc gga tcg ggt aag tct     144
Lys Glu Lys Val Ile Phe Val Met Gly Ala Thr Gly Ser Gly Lys Ser
         35                  40                  45 cgt ctc gcc atc gac cta gca act cgt ttt caa gga gag atc ata aac     192
Arg Leu Ala Ile Asp Leu Ala Thr Arg Phe Gln Gly Glu Ile Ile Asn
     50                  55                  60 tcc gac aag att caa ctt tac aag ggc cta gac gtc cta aca aac aaa     240
Ser Asp Lys Ile Gln Leu Tyr Lys Gly Leu Asp Val Leu Thr Asn Lys
 65                  70                  75                  80 gtc acc cct aaa gaa tgc cga ggc gtg cct cac cac ttg ctt gga gta     288
Val Thr Pro Lys Glu Cys Arg Gly Val Pro His His Leu Leu Gly Val
                 85                  90                  95 ttc gac tcc gaa gcc gga aac cta acg gcc acc cag tat agc cgc ctt     336
Phe Asp Ser Glu Ala Gly Asn Leu Thr Ala Thr Gln Tyr Ser Arg Leu
            100                 105                 110 gcg tca caa gca atc tcg aaa ctc tca gcg aac aac aag ctt ccc ata     384
Ala Ser Gln Ala Ile Ser Lys Leu Ser Ala Asn Asn Lys Leu Pro Ile
        115                 120                 125 gta gcc ggt gga tca aac tct tac atc gaa gca ctt gtt aat cat tcc     432
Val Ala Gly Gly Ser Asn Ser Tyr Ile Glu Ala Leu Val Asn His Ser
    130                 135                 140 tcg ggg ttt tta tta aac aac tac gat tgt tgt ttc att tgg gtc gac     480
Ser Gly Phe Leu Leu Asn Asn Tyr Asp Cys Cys Phe Ile Trp Val Asp
145                 150                 155                 160 gtt tcc tta ccc gta ctt aac tcc ttt gtc tca aaa cgt gtc gac cgc     528
Val Ser Leu Pro Val Leu Asn Ser Phe Val Ser Lys Arg Val Asp Arg
                165                 170                 175 atg atg gaa gca gga tta ctc gaa gaa gta aga gaa gtg ttc aat cca     576
```

```
                                     -continued

Met Met Glu Ala Gly Leu Leu Glu Glu Val Arg Glu Val Phe Asn Pro
            180                 185                 190 aaa gcg aat tac tcc gta ggg ata cga cga gct atc gga gtc ccc gag      624
Lys Ala Asn Tyr Ser Val Gly Ile Arg Arg Ala Ile Gly Val Pro Glu
            195                 200                 205 ctc cat gaa tat tta cgt aac gaa tct cta gtg gac cgt gcc aca aaa      672
Leu His Glu Tyr Leu Arg Asn Glu Ser Leu Val Asp Arg Ala Thr Lys
            210                 215                 220 agt aaa atg ctt gac gta gcc gtt aaa aat atc aaa aag aac act gag      720
Ser Lys Met Leu Asp Val Ala Val Lys Asn Ile Lys Lys Asn Thr Glu
225                 230                 235                 240 att tta gct tgt cga cag tta aaa aag att caa cgg ctt cac aag aag      768
Ile Leu Ala Cys Arg Gln Leu Lys Lys Ile Gln Arg Leu His Lys Lys
                245                 250                 255 tgg aag atg tct atg cat cgt gtt gac gcc act gag gtg ttc ttg aaa      816
Trp Lys Met Ser Met His Arg Val Asp Ala Thr Glu Val Phe Leu Lys
            260                 265                 270 cgc aac gta gaa gaa caa gac gag gct tgg gag aat ctt gta gcg aga      864
Arg Asn Val Glu Glu Gln Asp Glu Ala Trp Glu Asn Leu Val Ala Arg
            275                 280                 285 cca agc gag aga atc gtc gat aag ttt tat aat aat aat aac caa ctg      912
Pro Ser Glu Arg Ile Val Asp Lys Phe Tyr Asn Asn Asn Asn Gln Leu
            290                 295                 300 aaa aat gat gat gtt gag cac tgt ttg gcg gca tct tac ggc gga gga      960
Lys Asn Asp Asp Val Glu His Cys Leu Ala Ala Ser Tyr Gly Gly Gly
305                 310                 315                 320 agt gga agt aga gcc cac aat atg ata tga                              990
Ser Gly Ser Arg Ala His Asn Met Ile
            325

<210> SEQ ID NO 8
<211> LENGTH: 329
<212> TYPE: PRT
<213> ORGANISM: Arabidopsis thaliana

<400> SEQUENCE: 8

Met Lys Phe Ser Ile Ser Ser Leu Lys Gln Val Gln Pro Ile Leu Cys
1               5                   10                  15

Phe Lys Asn Lys Leu Ser Lys Val Asn Val Asn Ser Phe Leu His Pro
                20                  25                  30

Lys Glu Lys Val Ile Phe Val Met Gly Ala Thr Gly Ser Gly Lys Ser
            35                  40                  45

Arg Leu Ala Ile Asp Leu Ala Thr Arg Phe Gln Gly Glu Ile Ile Asn
        50                  55                  60

Ser Asp Lys Ile Gln Leu Tyr Lys Gly Leu Asp Val Leu Thr Asn Lys
65                  70                  75                  80

Val Thr Pro Lys Glu Cys Arg Gly Val Pro His His Leu Leu Gly Val
                85                  90                  95

Phe Asp Ser Glu Ala Gly Asn Leu Thr Ala Thr Gln Tyr Ser Arg Leu
            100                 105                 110

Ala Ser Gln Ala Ile Ser Lys Leu Ser Ala Asn Asn Lys Leu Pro Ile
        115                 120                 125

Val Ala Gly Gly Ser Asn Ser Tyr Ile Glu Ala Leu Val Asn His Ser
130                 135                 140

Ser Gly Phe Leu Leu Asn Asn Tyr Asp Cys Cys Phe Ile Trp Val Asp
145                 150                 155                 160

Val Ser Leu Pro Val Leu Asn Ser Phe Val Ser Lys Arg Val Asp Arg
                165                 170                 175
```

```
Met Met Glu Ala Gly Leu Leu Glu Glu Val Arg Glu Val Phe Asn Pro
            180                 185                 190

Lys Ala Asn Tyr Ser Val Gly Ile Arg Arg Ala Ile Gly Val Pro Glu
            195                 200                 205

Leu His Glu Tyr Leu Arg Asn Glu Ser Leu Val Asp Arg Ala Thr Lys
            210                 215                 220

Ser Lys Met Leu Asp Val Ala Val Lys Asn Ile Lys Lys Asn Thr Glu
225                 230                 235                 240

Ile Leu Ala Cys Arg Gln Leu Lys Lys Ile Gln Arg Leu His Lys Lys
                245                 250                 255

Trp Lys Met Ser Met His Arg Val Asp Ala Thr Glu Val Phe Leu Lys
                260                 265                 270

Arg Asn Val Glu Glu Gln Asp Glu Ala Trp Glu Asn Leu Val Ala Arg
            275                 280                 285

Pro Ser Glu Arg Ile Val Asp Lys Phe Tyr Asn Asn Asn Gln Leu
            290                 295                 300

Lys Asn Asp Asp Val Glu His Cys Leu Ala Ala Ser Tyr Gly Gly Gly
305                 310                 315                 320

Ser Gly Ser Arg Ala His Asn Met Ile
                325

<210> SEQ ID NO 9
<211> LENGTH: 993
<212> TYPE: DNA
<213> ORGANISM: Arabidopsis thaliana
<220> FEATURE:
<221> NAME/KEY: CDS
<222> LOCATION: (1)..(990)

<400> SEQUENCE: 9 atg caa aat ctt acg tcc aca ttc gtc tct cct tcc atg atc ccg atc      48
Met Gln Asn Leu Thr Ser Thr Phe Val Ser Pro Ser Met Ile Pro Ile
  1               5                  10                  15 act tct ccg cgg ctg cga ctg cca cca cca cga tca gta gtt ccc atg      96
Thr Ser Pro Arg Leu Arg Leu Pro Pro Pro Arg Ser Val Val Pro Met
                 20                  25                  30 act acc gtt tgc atg gaa caa tca tac aag caa aaa gtg gtt gtg atc     144
Thr Thr Val Cys Met Glu Gln Ser Tyr Lys Gln Lys Val Val Val Ile
             35                  40                  45 atg gga gcc acc gga tca ggc aag tca tgc ctc tca atc gat cta gca     192
Met Gly Ala Thr Gly Ser Gly Lys Ser Cys Leu Ser Ile Asp Leu Ala
 50                  55                  60 act cgt ttc tct ggc gag atc gtc aat tcc gac aag att caa ttc tac     240
Thr Arg Phe Ser Gly Glu Ile Val Asn Ser Asp Lys Ile Gln Phe Tyr
 65                  70                  75                  80 gat gga ttg aag gtc act acg aat caa atg agc atc ctt gag aga tgt     288
Asp Gly Leu Lys Val Thr Thr Asn Gln Met Ser Ile Leu Glu Arg Cys
                 85                  90                  95 gga gtc cct cac cat ctc ctt ggt gag ctc cct ccg gat gat agc gaa     336
Gly Val Pro His His Leu Leu Gly Glu Leu Pro Pro Asp Asp Ser Glu
                100                 105                 110 cta act acc tcc gaa ttc cgc tct ttg gcg tcg cgg tcc atc tcc gag     384
Leu Thr Thr Ser Glu Phe Arg Ser Leu Ala Ser Arg Ser Ile Ser Glu
            115                 120                 125 att act gct cgt gga aac ctc ccg att ata gct ggt gga tca aac tcc     432
Ile Thr Ala Arg Gly Asn Leu Pro Ile Ile Ala Gly Gly Ser Asn Ser
130                 135                 140 ttc att cat gct ctc ctt gtc gac cgt ttt gac ccc aaa acc tat cca     480
```

```
Phe Ile His Ala Leu Leu Val Asp Arg Phe Asp Pro Lys Thr Tyr Pro
145                 150                 155                 160 ttc tct tct gag aca tcc atc tct tcc ggc ttg agg tac gag tgt tgc      528
Phe Ser Ser Glu Thr Ser Ile Ser Ser Gly Leu Arg Tyr Glu Cys Cys
                    165                 170                 175 ttc ctt tgg gtg gat gtc tca gtg tcg gtc ctg ttc gag tac ctc tcg      576
Phe Leu Trp Val Asp Val Ser Val Ser Val Leu Phe Glu Tyr Leu Ser
                180                 185                 190 aaa cgt gtc gac cag atg atg gag tca ggg atg ttc gag gag cta gcc      624
Lys Arg Val Asp Gln Met Met Glu Ser Gly Met Phe Glu Glu Leu Ala
            195                 200                 205 ggt ttc tac gac ccg aga tat tcc ggg tcc gca atc cga gcc cac ggg      672
Gly Phe Tyr Asp Pro Arg Tyr Ser Gly Ser Ala Ile Arg Ala His Gly
210                 215                 220 att cac aag acc ata gga ata ccc gag ttc gac cgg tac ttc agc tta      720
Ile His Lys Thr Ile Gly Ile Pro Glu Phe Asp Arg Tyr Phe Ser Leu
225                 230                 235                 240 tac ccg cct gag aga aag cag aag atg tcc gaa tgg gac caa gca aga      768
Tyr Pro Pro Glu Arg Lys Gln Lys Met Ser Glu Trp Asp Gln Ala Arg
                245                 250                 255 aag ggg gcg tat gac gaa gct gtc caa gag atc aaa gag aac aca tgg      816
Lys Gly Ala Tyr Asp Glu Ala Val Gln Glu Ile Lys Glu Asn Thr Trp
            260                 265                 270 agg ctt gcg aag aag cag att gag agg atc atg aag ctg aaa agc agc      864
Arg Leu Ala Lys Lys Gln Ile Glu Arg Ile Met Lys Leu Lys Ser Ser
        275                 280                 285 gga tgg gac att cag agg ttg gac gct acg ccg tca ttt gga aga tcg      912
Gly Trp Asp Ile Gln Arg Leu Asp Ala Thr Pro Ser Phe Gly Arg Ser
290                 295                 300 tca aga gag att tgg gac aat act gtt ttg gat gaa agc atc aag gtt      960
Ser Arg Glu Ile Trp Asp Asn Thr Val Leu Asp Glu Ser Ile Lys Val
305                 310                 315                 320 gtg aaa cgc ttc ttg gtg aaa gac aaa gtg tga                          993
Val Lys Arg Phe Leu Val Lys Asp Lys Val
                325                 330

<210> SEQ ID NO 10
<211> LENGTH: 330
<212> TYPE: PRT
<213> ORGANISM: Arabidopsis thaliana

<400> SEQUENCE: 10

Met Gln Asn Leu Thr Ser Thr Phe Val Ser Pro Ser Met Ile Pro Ile
1               5                   10                  15

Thr Ser Pro Arg Leu Arg Leu Pro Pro Arg Ser Val Val Pro Met
            20                  25                  30

Thr Thr Val Cys Met Glu Gln Ser Tyr Lys Gln Lys Val Val Ile
        35                  40                  45

Met Gly Ala Thr Gly Ser Gly Lys Ser Cys Leu Ser Ile Asp Leu Ala
    50                  55                  60

Thr Arg Phe Ser Gly Glu Ile Val Asn Ser Asp Lys Ile Gln Phe Tyr
65                  70                  75                  80

Asp Gly Leu Lys Val Thr Thr Asn Gln Met Ser Ile Leu Glu Arg Cys
                85                  90                  95

Gly Val Pro His His Leu Leu Gly Glu Leu Pro Pro Asp Asp Ser Glu
            100                 105                 110

Leu Thr Thr Ser Glu Phe Arg Ser Leu Ala Ser Arg Ser Ile Ser Glu
        115                 120                 125
```

```
Ile Thr Ala Arg Gly Asn Leu Pro Ile Ile Ala Gly Gly Ser Asn Ser
    130                 135                 140
Phe Ile His Ala Leu Leu Val Asp Arg Phe Asp Pro Lys Thr Tyr Pro
145                 150                 155                 160
Phe Ser Ser Glu Thr Ser Ile Ser Ser Gly Leu Arg Tyr Glu Cys Cys
                165                 170                 175
Phe Leu Trp Val Asp Val Ser Val Ser Val Leu Phe Glu Tyr Leu Ser
            180                 185                 190
Lys Arg Val Asp Gln Met Met Glu Ser Gly Met Phe Glu Glu Leu Ala
        195                 200                 205
Gly Phe Tyr Asp Pro Arg Tyr Ser Gly Ser Ala Ile Arg Ala His Gly
    210                 215                 220
Ile His Lys Thr Ile Gly Ile Pro Glu Phe Asp Arg Tyr Phe Ser Leu
225                 230                 235                 240
Tyr Pro Pro Glu Arg Lys Gln Lys Met Ser Glu Trp Asp Gln Ala Arg
                245                 250                 255
Lys Gly Ala Tyr Asp Glu Ala Val Gln Glu Ile Lys Glu Asn Thr Trp
            260                 265                 270
Arg Leu Ala Lys Lys Gln Ile Glu Arg Ile Met Lys Leu Lys Ser Ser
        275                 280                 285
Gly Trp Asp Ile Gln Arg Leu Asp Ala Thr Pro Ser Phe Gly Arg Ser
    290                 295                 300
Ser Arg Glu Ile Trp Asp Asn Thr Val Leu Asp Glu Ser Ile Lys Val
305                 310                 315                 320
Val Lys Arg Phe Leu Val Lys Asp Lys Val
                325                 330

<210> SEQ ID NO 11
<211> LENGTH: 1071
<212> TYPE: DNA
<213> ORGANISM: Arabidopsis thaliana
<220> FEATURE:
<221> NAME/KEY: CDS
<222> LOCATION: (1)..(1071)

<400> SEQUENCE: 11 atg aca gaa ctc aac ttc cac ctc ctc cca ata atc tcc gat cgc ttc      48
Met Thr Glu Leu Asn Phe His Leu Leu Pro Ile Ile Ser Asp Arg Phe
  1               5                  10                  15 acg acg acg acg aca aca tca ccg tcg ttc tcg tca cat tct tct tct      96
Thr Thr Thr Thr Thr Thr Ser Pro Ser Phe Ser Ser His Ser Ser Ser
             20                  25                  30 tct tct tct ctt ctc tct ttc acc aaa cga aga cga aaa cac caa cct     144
Ser Ser Ser Leu Leu Ser Phe Thr Lys Arg Arg Arg Lys His Gln Pro
         35                  40                  45 tta gta tca tcc ata cgc atg gaa cag tca cgg tca cgg aat cgg aaa     192
Leu Val Ser Ser Ile Arg Met Glu Gln Ser Arg Ser Arg Asn Arg Lys
     50                  55                  60 gac aaa gtc gtc gtc att tta gga gca acc ggc gcc gga aaa tca aga     240
Asp Lys Val Val Val Ile Leu Gly Ala Thr Gly Ala Gly Lys Ser Arg
 65                  70                  75                  80 ctt tcc gtc gat ctc gct act cgt ttc cct tca gag atc ata aac tcc     288
Leu Ser Val Asp Leu Ala Thr Arg Phe Pro Ser Glu Ile Ile Asn Ser
                 85                  90                  95 gat aaa atc caa gtc tac gaa gga tta gag atc aca acg aat cag att     336
Asp Lys Ile Gln Val Tyr Glu Gly Leu Glu Ile Thr Thr Asn Gln Ile
            100                 105                 110 acg tta caa gac cgt cgc ggc gtt cct cac cat ctc ctc ggc gtc atc     384
```

```
                Thr Leu Gln Asp Arg Arg Gly Val Pro His His Leu Leu Gly Val Ile
                    115                 120                 125 aac ccc gaa cac ggc gaa cta acc gcc gga gag ttt cgc tcc gcc gct                432
Asn Pro Glu His Gly Glu Leu Thr Ala Gly Glu Phe Arg Ser Ala Ala
    130                 135                 140 tca aac gtc gtc aaa gag ata act tct cgt caa aag gtt ccg att atc                480
Ser Asn Val Val Lys Glu Ile Thr Ser Arg Gln Lys Val Pro Ile Ile
145                 150                 155                 160 gcc ggt gga tct aac tct ttc gtc cac gca ctc tta gct caa cga ttc                528
Ala Gly Gly Ser Asn Ser Phe Val His Ala Leu Leu Ala Gln Arg Phe
                165                 170                 175 gac cca aag ttc gat cct ttt tca tcc ggg tcg tgt tta atc agc tcc                576
Asp Pro Lys Phe Asp Pro Phe Ser Ser Gly Ser Cys Leu Ile Ser Ser
            180                 185                 190 gat ttg cgt tac gag tgt tgt ttc atc tgg gtc gat gta tcg gag act                624
Asp Leu Arg Tyr Glu Cys Cys Phe Ile Trp Val Asp Val Ser Glu Thr
        195                 200                 205 gtt ctc tac gag tat ctt ctc aga aga gtc gac gaa atg atg gat tca                672
Val Leu Tyr Glu Tyr Leu Leu Arg Arg Val Asp Glu Met Met Asp Ser
    210                 215                 220 ggt atg ttc gaa gag ctg tct aga ttc tac gac ccg gtt aaa tcc ggt                720
Gly Met Phe Glu Glu Leu Ser Arg Phe Tyr Asp Pro Val Lys Ser Gly
225                 230                 235                 240 tta gaa acc cgg ttt ggg att agg aaa gct ata ggt gta ccg gag ttt                768
Leu Glu Thr Arg Phe Gly Ile Arg Lys Ala Ile Gly Val Pro Glu Phe
                245                 250                 255 gac ggt tac ttc aaa gag tat cca ccg gag aag aag atg ata aag tgg                816
Asp Gly Tyr Phe Lys Glu Tyr Pro Pro Glu Lys Lys Met Ile Lys Trp
            260                 265                 270 gac gct tta aga aaa gcg gcg tac gat aag gcg gtt gat gat atc aaa                864
Asp Ala Leu Arg Lys Ala Ala Tyr Asp Lys Ala Val Asp Asp Ile Lys
        275                 280                 285 agg aac acg tgg acg tta gcg aag aga caa gtg aag aag att gag atg                912
Arg Asn Thr Trp Thr Leu Ala Lys Arg Gln Val Lys Lys Ile Glu Met
    290                 295                 300 cta aaa gac gct ggt tgg gaa ata gaa aga gtt gat gca acg gcg tcg                960
Leu Lys Asp Ala Gly Trp Glu Ile Glu Arg Val Asp Ala Thr Ala Ser
305                 310                 315                 320 ttt aaa gca gtg atg atg aag agt tcg tcg gag aag aag tgg aga gag               1008
Phe Lys Ala Val Met Met Lys Ser Ser Ser Glu Lys Lys Trp Arg Glu
                325                 330                 335 aat tgg gaa gag caa gtg ttg gag cca agc gta aag att gtg aag cgg               1056
Asn Trp Glu Glu Gln Val Leu Glu Pro Ser Val Lys Ile Val Lys Arg
            340                 345                 350 cat ttg gtg caa aat                                                           1071
His Leu Val Gln Asn
        355

<210> SEQ ID NO 12
<211> LENGTH: 357
<212> TYPE: PRT
<213> ORGANISM: Arabidopsis thaliana

<400> SEQUENCE: 12

Met Thr Glu Leu Asn Phe His Leu Leu Pro Ile Ile Ser Asp Arg Phe
1               5                   10                  15

Thr Thr Thr Thr Thr Thr Ser Pro Ser Phe Ser Ser His Ser Ser Ser
                20                  25                  30

Ser Ser Ser Leu Leu Ser Phe Thr Lys Arg Arg Arg Lys His Gln Pro
            35                  40                  45
```

```
Leu Val Ser Ser Ile Arg Met Glu Gln Ser Arg Ser Arg Asn Arg Lys
    50                  55                  60

Asp Lys Val Val Val Ile Leu Gly Ala Thr Gly Ala Gly Lys Ser Arg
 65                  70                  75                  80

Leu Ser Val Asp Leu Ala Thr Arg Phe Pro Ser Glu Ile Ile Asn Ser
                 85                  90                  95

Asp Lys Ile Gln Val Tyr Glu Gly Leu Glu Ile Thr Thr Asn Gln Ile
                100                 105                 110

Thr Leu Gln Asp Arg Arg Gly Val Pro His His Leu Leu Gly Val Ile
            115                 120                 125

Asn Pro Glu His Gly Glu Leu Thr Ala Gly Glu Phe Arg Ser Ala Ala
        130                 135                 140

Ser Asn Val Val Lys Glu Ile Thr Ser Arg Gln Lys Val Pro Ile Ile
145                 150                 155                 160

Ala Gly Gly Ser Asn Ser Phe Val His Ala Leu Leu Ala Gln Arg Phe
                165                 170                 175

Asp Pro Lys Phe Asp Pro Phe Ser Ser Gly Ser Cys Leu Ile Ser Ser
            180                 185                 190

Asp Leu Arg Tyr Glu Cys Cys Phe Ile Trp Val Asp Val Ser Glu Thr
        195                 200                 205

Val Leu Tyr Glu Tyr Leu Leu Arg Arg Val Asp Glu Met Met Asp Ser
    210                 215                 220

Gly Met Phe Glu Glu Leu Ser Arg Phe Tyr Asp Pro Val Lys Ser Gly
225                 230                 235                 240

Leu Glu Thr Arg Phe Gly Ile Arg Lys Ala Ile Gly Val Pro Glu Phe
                245                 250                 255

Asp Gly Tyr Phe Lys Glu Tyr Pro Pro Glu Lys Lys Met Ile Lys Trp
            260                 265                 270

Asp Ala Leu Arg Lys Ala Ala Tyr Asp Lys Ala Val Asp Asp Ile Lys
        275                 280                 285

Arg Asn Thr Trp Thr Leu Ala Lys Arg Gln Val Lys Lys Ile Glu Met
    290                 295                 300

Leu Lys Asp Ala Gly Trp Glu Ile Glu Arg Val Asp Ala Thr Ala Ser
305                 310                 315                 320

Phe Lys Ala Val Met Met Lys Ser Ser Ser Glu Lys Lys Trp Arg Glu
                325                 330                 335

Asn Trp Glu Glu Gln Val Leu Glu Pro Ser Val Lys Ile Val Lys Arg
            340                 345                 350

His Leu Val Gln Asn
        355

<210> SEQ ID NO 13
<211> LENGTH: 1029
<212> TYPE: DNA
<213> ORGANISM: Arabidopsis thaliana
<220> FEATURE:
<221> NAME/KEY: CDS
<222> LOCATION: (1)..(1026)

<400> SEQUENCE: 13 atg caa caa ctc atg acc ttg tta tca cca cca ctc tct cat tct tct    48
Met Gln Gln Leu Met Thr Leu Leu Ser Pro Pro Leu Ser His Ser Ser
 1               5                  10                  15 ctc ctt ccc acc gtc act acc aaa ttc ggg tca cca cga tta gtc act    96
Leu Leu Pro Thr Val Thr Thr Lys Phe Gly Ser Pro Arg Leu Val Thr
            20                  25                  30
```

```
                                              -continued acg tgc atg ggc cat gca ggg cgt aaa aat atc aag gat aag gtg gtt       144
Thr Cys Met Gly His Ala Gly Arg Lys Asn Ile Lys Asp Lys Val Val
         35                  40                  45 ctc atc aca ggt aca aca ggc aca ggc aag tca cgc ctc tca gtc gat       192
Leu Ile Thr Gly Thr Thr Gly Thr Gly Lys Ser Arg Leu Ser Val Asp
 50                  55                  60 ctt gcc acc cgt ttt ttt ccc gcc gag atc ata aac tcg gac aaa atg       240
Leu Ala Thr Arg Phe Phe Pro Ala Glu Ile Ile Asn Ser Asp Lys Met
 65                  70                  75                  80 caa atc tac aag gga ttc gag att gtc aca aat cta atc cca ctg cat       288
Gln Ile Tyr Lys Gly Phe Glu Ile Val Thr Asn Leu Ile Pro Leu His
                 85                  90                  95 gag caa gga gga gtc ccg cac cat ctt cta ggt cag ttc cac cca caa       336
Glu Gln Gly Gly Val Pro His His Leu Leu Gly Gln Phe His Pro Gln
            100                 105                 110 gac ggt gaa ctc acc cct gca gag ttc cgt tct ttg gcg aca ctg tcc       384
Asp Gly Glu Leu Thr Pro Ala Glu Phe Arg Ser Leu Ala Thr Leu Ser
        115                 120                 125 atc tct aaa cta att tct agc aag aaa ctc ccg att gta gtt ggt gga       432
Ile Ser Lys Leu Ile Ser Ser Lys Lys Leu Pro Ile Val Val Gly Gly
130                 135                 140 tcc aac tcc ttc aat cac gct cta ctc gcc gag cgt ttt gac ccg gat       480
Ser Asn Ser Phe Asn His Ala Leu Leu Ala Glu Arg Phe Asp Pro Asp
145                 150                 155                 160 att gat cca ttc tct ccc gga tcg agt ctt tca acg atc tgc tct gac       528
Ile Asp Pro Phe Ser Pro Gly Ser Ser Leu Ser Thr Ile Cys Ser Asp
                165                 170                 175 cta agg tac aaa tgt tgc atc tta tgg gtt gat gtt tta gag ccg gtt       576
Leu Arg Tyr Lys Cys Cys Ile Leu Trp Val Asp Val Leu Glu Pro Val
            180                 185                 190 ctg ttc caa cac ttg tgc aat cgt gtc gac caa atg atc gag tcg gga       624
Leu Phe Gln His Leu Cys Asn Arg Val Asp Gln Met Ile Glu Ser Gly
        195                 200                 205 ttg gtc gag cag ctt gcc gaa ttg tac gac cct gtt gta gat tcg ggt       672
Leu Val Glu Gln Leu Ala Glu Leu Tyr Asp Pro Val Val Asp Ser Gly
    210                 215                 220 cga cga cta ggg gtt cgg aag acg ata gga gta gag gag ttc gac cga       720
Arg Arg Leu Gly Val Arg Lys Thr Ile Gly Val Glu Glu Phe Asp Arg
225                 230                 235                 240 tac ttt aga gta tac cct aag gag atg gac aag gga att tgg gac tta       768
Tyr Phe Arg Val Tyr Pro Lys Glu Met Asp Lys Gly Ile Trp Asp Leu
                245                 250                 255 gcg aga aag gcg gcg tac gag gag aca gtg aag ggg atg aaa gag agg       816
Ala Arg Lys Ala Ala Tyr Glu Glu Thr Val Lys Gly Met Lys Glu Arg
            260                 265                 270 aca tgt cgg ttg gtg aag aag cag aaa gag aag atc atg aag ctg ata       864
Thr Cys Arg Leu Val Lys Lys Gln Lys Glu Lys Ile Met Lys Leu Ile
        275                 280                 285 aga ggt ggt tgg gag att aag agg ctt gac gct acg gcg gca att atg       912
Arg Gly Gly Trp Glu Ile Lys Arg Leu Asp Ala Thr Ala Ala Ile Met
    290                 295                 300 gct gag ctg aat caa agt acg gca aag gga gaa gga aag aat ggg aga       960
Ala Glu Leu Asn Gln Ser Thr Ala Lys Gly Glu Gly Lys Asn Gly Arg
305                 310                 315                 320 gag att tgg gaa aaa cac att gtg gat gaa agt gtc gag att gtc aag      1008
Glu Ile Trp Glu Lys His Ile Val Asp Glu Ser Val Glu Ile Val Lys
                325                 330                 335 aag ttt ttg ttg gaa gtt tag                                          1029
Lys Phe Leu Leu Glu Val
```

<210> SEQ ID NO 14
<211> LENGTH: 342
<212> TYPE: PRT
<213> ORGANISM: Arabidopsis thaliana

<400> SEQUENCE: 14

```
Met Gln Gln Leu Met Thr Leu Leu Ser Pro Leu Ser His Ser Ser
 1               5                  10                  15

Leu Leu Pro Thr Val Thr Thr Lys Phe Gly Pro Arg Leu Val Thr
            20                  25                  30

Thr Cys Met Gly His Ala Gly Arg Lys Asn Ile Lys Asp Lys Val Val
            35                  40                  45

Leu Ile Thr Gly Thr Thr Gly Thr Gly Lys Ser Arg Leu Ser Val Asp
 50                  55                  60

Leu Ala Thr Arg Phe Phe Pro Ala Glu Ile Ile Asn Ser Asp Lys Met
 65                  70                  75                  80

Gln Ile Tyr Lys Gly Phe Glu Ile Val Thr Asn Leu Ile Pro Leu His
                 85                  90                  95

Glu Gln Gly Gly Val Pro His His Leu Leu Gly Gln Phe His Pro Gln
            100                 105                 110

Asp Gly Glu Leu Thr Pro Ala Glu Phe Arg Ser Leu Ala Thr Leu Ser
            115                 120                 125

Ile Ser Lys Leu Ile Ser Ser Lys Lys Leu Pro Ile Val Val Gly Gly
            130                 135                 140

Ser Asn Ser Phe Asn His Ala Leu Leu Ala Glu Arg Phe Asp Pro Asp
145                 150                 155                 160

Ile Asp Pro Phe Ser Pro Gly Ser Ser Leu Ser Thr Ile Cys Ser Asp
                165                 170                 175

Leu Arg Tyr Lys Cys Cys Ile Leu Trp Val Asp Val Leu Glu Pro Val
            180                 185                 190

Leu Phe Gln His Leu Cys Asn Arg Val Asp Gln Met Ile Glu Ser Gly
            195                 200                 205

Leu Val Glu Gln Leu Ala Glu Leu Tyr Asp Pro Val Val Asp Ser Gly
            210                 215                 220

Arg Arg Leu Gly Val Arg Lys Thr Ile Gly Val Glu Glu Phe Asp Arg
225                 230                 235                 240

Tyr Phe Arg Val Tyr Pro Lys Glu Met Asp Lys Gly Ile Trp Asp Leu
                245                 250                 255

Ala Arg Lys Ala Ala Tyr Glu Glu Thr Val Lys Gly Met Lys Glu Arg
            260                 265                 270

Thr Cys Arg Leu Val Lys Lys Gln Glu Lys Ile Met Lys Leu Ile
            275                 280                 285

Arg Gly Gly Trp Glu Ile Lys Arg Leu Asp Ala Thr Ala Ile Met
            290                 295                 300

Ala Glu Leu Asn Gln Ser Thr Ala Lys Gly Glu Gly Lys Asn Gly Arg
305                 310                 315                 320

Glu Ile Trp Glu Lys His Ile Val Asp Glu Ser Val Glu Ile Val Lys
                325                 330                 335

Lys Phe Leu Leu Glu Val
            340
```

<210> SEQ ID NO 15
<211> LENGTH: 32

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcccccgggc gatgatgatg ttaaaccta gc                                    32

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcccccgggt caatttactt ctgcttcttg aacttc                               36

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaaatgaagt gtaatgacaa aatggttgtg                                      30

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtccaaacta gttaagactt aaaaatc                                         27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caccagcaag tttatattgc aaagcgt                                         27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttgtaacca cgtaaaagat aagggtg                                         27

<210> SEQ ID NO 21
<211> LENGTH: 35
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 21
ggaattccat atgaagtgta atgacaaaat ggttg                              35

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaagatctgt ccaaactagt taagacttaa aaatc                              35

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gatccccggc atatgatgat gttaaaccct agc                                33

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acggtaccca tatgtcaatt tacttctgct tcttgaac                            38

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttatacatat gaagccatgc atgacggctc tag                                33

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgggatcctc accgggaaat cgccgcca                                      28

<210> SEQ ID NO 27
<211> LENGTH: 46
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 27
ctcgagttgg cgcgccaccc gggattaatt aagactagtg gggtac                    46

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cccactagtc ttaattaatc ccgggtggcg cgccaactcg ag                        42

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgacagaac tcaacttcca cct                                             23

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caaaaaaaag atctaatttt gcaccaaatg ccgctt                               36

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
attatgcaaa atcttacgtc cacattcgtc                                      30

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acaggatcct cacactttgt ctttcaccaa g                                    31

<210> SEQ ID NO 33
<211> LENGTH: 31
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 33
ccgctcgaga tgaagccatg catgacggct c                                      31

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggactagtca ccgggaaatc gccgcca                                           27

<210> SEQ ID NO 35
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (2)
<223> OTHER INFORMATION: Variable amino acid
<220> FEATURE:
<221> NAME/KEY: VARIANT
<222> LOCATION: (4)..(5)
<223> OTHER INFORMATION: Variable amino acid
<220> FEATURE:
<221> NAME/KEY: VARIANT
<222> LOCATION: (8)
<223> OTHER INFORMATION: Ser or Thr
<220> FEATURE:
<221> NAME/KEY: VARIANT
<222> LOCATION: (9)..(13)
<223> OTHER INFORMATION: Variable amino acid
<220> FEATURE:
<221> NAME/KEY: VARIANT
<222> LOCATION: (14)
<223> OTHER INFORMATION: Val, Leu or Ile
<220> FEATURE:
<221> NAME/KEY: VARIANT
<222> LOCATION: (15)..(21)
<223> OTHER INFORMATION: Variable amino acid
<220> FEATURE:
<221> NAME/KEY: VARIANT
<222> LOCATION: (22)..(23)
<223> OTHER INFORMATION: Val, Leu or Ile
<220> FEATURE:
<221> NAME/KEY: VARIANT
<222> LOCATION: (24)..(25)
<223> OTHER INFORMATION: Variable amino acid
<220> FEATURE:
<221> NAME/KEY: VARIANT
<222> LOCATION: (27)..(28)
<223> OTHER INFORMATION: Variable amino acid
<220> FEATURE:
<221> NAME/KEY: VARIANT
<222> LOCATION: (30)
<223> OTHER INFORMATION: Variable amino acid
<220> FEATURE:
<221> NAME/KEY: VARIANT
<222> LOCATION: (31)..(90)
<223> OTHER INFORMATION: This region may encompass 57-60 variable
      residues
<220> FEATURE:
<221> NAME/KEY: VARIANT
<222> LOCATION: (91)..(92)
<223> OTHER INFORMATION: Val, Leu or Ile
<220> FEATURE:
<221> NAME/KEY: VARIANT

```
<222> LOCATION: (93)
<223> OTHER INFORMATION: Variable amino acid
<220> FEATURE:
<221> NAME/KEY: VARIANT
<222> LOCATION: (96)
<223> OTHER INFORMATION: Ser or Thr

<400> SEQUENCE: 35

Gly Xaa Thr Xaa Xaa Gly Lys Xaa Xaa Xaa Xaa Xaa Xaa Xaa Xaa
 1               5                  10                  15

Xaa Xaa Xaa Xaa Xaa Xaa Xaa Xaa Xaa Asp Xaa Xaa Gln Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Gly Gly Xaa
                85                  90                  95
```